(12) United States Patent
Okazaki

(10) Patent No.: US 11,172,807 B2
(45) Date of Patent: Nov. 16, 2021

(54) ENDOSCOPE DEVICE AND ENDOSCOPE SYSTEM WITH DEFORMING INSERTION PORTION WIRE

(71) Applicant: OLYMPUS CORPORATION, Tokyo (JP)

(72) Inventor: Yoshiro Okazaki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 387 days.

(21) Appl. No.: 16/192,916

(22) Filed: Nov. 16, 2018

(65) Prior Publication Data

US 2019/0082939 A1 Mar. 21, 2019

Related U.S. Application Data

(63) Continuation of application No. PCT/JP2016/065222, filed on May 23, 2016.

(51) Int. Cl.
*A61B 1/00* (2006.01)
*A61B 1/005* (2006.01)

(52) U.S. Cl.
CPC ........ *A61B 1/00142* (2013.01); *A61B 1/0055* (2013.01); *A61B 1/0057* (2013.01);
(Continued)

(58) Field of Classification Search
CPC ............ A61B 1/00142; A61B 1/00087; A61B 1/00154; A61B 1/0055; A61B 1/0057;
(Continued)

(56) References Cited

U.S. PATENT DOCUMENTS 5,074,840 A 12/1991 Yoon
5,156,151 A 10/1992 Imran
(Continued)

FOREIGN PATENT DOCUMENTS

EP 0499491 A2 8/1992
EP 0771547 A2 5/1997
(Continued)

OTHER PUBLICATIONS

International Search Report dated Jul. 19, 2016 issued in PCT/JP2016/065222.

*Primary Examiner* — Timothy J Neal
*Assistant Examiner* — William B Chou
(74) *Attorney, Agent, or Firm* — Scully, Scott, Murphy & Presser, P.C.

(57) ABSTRACT

An endoscope device is provided with: an elongated sheath having an endoscope insertion passage that penetrates therethrough in the longitudinal direction and into which an endoscope is inserted; and a wire that is provided in the sheath and that has a bending portion that bends toward the endoscope insertion passage, wherein the wire has a deforming region that is provided in a distal end portion of the sheath and that deforms between a normal form, in which the deforming region is disposed in the interior of the sheath or along an outer circumferential surface thereof, and a loop-shaped expanded form, in which the bending portion is bended and has a diameter larger than the outer diameter of the sheath.

9 Claims, 14 Drawing Sheets

(52) U.S. Cl.
CPC ...... *A61B 1/00087* (2013.01); *A61B 1/00154* (2013.01); *A61B 1/0052* (2013.01); *A61B 1/00135* (2013.01); *A61B 1/00174* (2013.01)

(58) Field of Classification Search
CPC ............ A61B 1/00135; A61B 1/00174; A61B 1/0052
See application file for complete search history.

(56) References Cited

U.S. PATENT DOCUMENTS

| | | | |
|---|---|---|---|
| 5,228,442 A | 7/1993 | Imran | |
| 5,239,999 A | 8/1993 | Imran | |
| 5,279,299 A | 1/1994 | Imran | |
| 5,327,889 A | 7/1994 | Imran | |
| 5,345,936 A | 9/1994 | Pomeranz et al. | |
| 5,374,261 A | 12/1994 | Yoon | |
| 5,392,787 A | 2/1995 | Yoon | |
| 5,404,638 A | 4/1995 | Imran | |
| 5,406,946 A | 4/1995 | Imran | |
| 5,407,423 A | 4/1995 | Yoon | |
| 5,415,166 A | 5/1995 | Imran | |
| 5,451,204 A | 5/1995 | Imran | |
| 5,425,364 A | 6/1995 | Imran | |
| 5,439,457 A | 8/1995 | Yoon | |
| 5,456,254 A | 10/1995 | Pietroski et al. | |
| 5,465,717 A | 11/1995 | Imran et al. | |
| 5,484,426 A | 1/1996 | Yoon | |
| 5,514,085 A | 5/1996 | Yoon | |
| 5,514,091 A | 5/1996 | Yoon | |
| 5,556,376 A | 9/1996 | Yoon | |
| 5,599,292 A | 2/1997 | Yoon | |
| 5,613,950 A | 3/1997 | Yoon | |
| 5,649,902 A | 7/1997 | Yoon | |
| 5,656,013 A | 8/1997 | Yoon | |
| 5,700,239 A | 12/1997 | Yoon | |
| 5,716,321 A | 2/1998 | Kerin et al. | |
| 5,730,725 A | 3/1998 | Yoon | |
| 5,733,252 A | 3/1998 | Yoon | |
| 5,738,683 A * | 4/1998 | Osypka ................... | A61L 29/02 606/47 |
| 5,755,724 A | 5/1998 | Yoon | |
| 5,782,800 A | 7/1998 | Yoon | |
| 5,800,394 A | 9/1998 | Yoon et al. | |
| 5,823,947 A | 10/1998 | Yoon et al. | |
| 5,836,953 A | 11/1998 | Yoon | |
| 5,873,815 A | 2/1999 | Kerin et al. | |
| 5,935,056 A | 8/1999 | Kerin et al. | |
| 6,120,437 A | 9/2000 | Yoon et al. | |
| 6,142,994 A * | 11/2000 | Swanson ............ | A61B 18/1482 606/41 |
| 6,196,966 B1 | 3/2001 | Kerin et al. | |
| 7,704,249 B2 * | 4/2010 | Woloszko ............ | A61B 18/149 606/48 |
| 7,930,016 B1 | 4/2011 | Saadat | |
| 2004/0064138 A1 | 4/2004 | Grabek | |
| 2004/0111019 A1 | 6/2004 | Long | |
| 2004/0111020 A1 | 6/2004 | Long | |
| 2004/0199087 A1 | 10/2004 | Swain et al. | |
| 2004/0199088 A1 | 10/2004 | Bakos et al. | |
| 2006/0015136 A1 * | 1/2006 | Besselink ................. | A61F 2/01 606/200 |
| 2006/0184048 A1 | 8/2006 | Saadat | |
| 2007/0167828 A1 | 7/2007 | Saadat | |
| 2007/0287886 A1 | 12/2007 | Saadat | |
| 2008/0004606 A1 | 1/2008 | Swain et al. | |
| 2008/0015445 A1 | 1/2008 | Saadat et al. | |
| 2008/0033290 A1 | 2/2008 | Saadat et al. | |
| 2008/0058591 A1 | 3/2008 | Saadat et al. | |
| 2008/0188759 A1 | 8/2008 | Saadat et al. | |
| 2008/0281293 A1 | 11/2008 | Peh et al. | |
| 2009/0054803 A1 | 2/2009 | Saadat et al. | |
| 2009/0275799 A1 | 11/2009 | Saadat et al. | |
| 2009/0275842 A1 | 11/2009 | Saadat et al. | |
| 2009/0281374 A1 | 11/2009 | Leanna et al. | |
| 2009/0299363 A1 | 12/2009 | Saadat et al. | |
| 2010/0010311 A1 | 1/2010 | Miller et al. | |
| 2010/0240952 A1 | 9/2010 | Okazaki et al. | |
| 2010/0280539 A1 | 11/2010 | Miyoshi et al. | |
| 2010/0292558 A1 | 11/2010 | Saadat et al. | |
| 2010/0331619 A1 | 12/2010 | Miyoshi et al. | |
| 2011/0071342 A1 | 3/2011 | Okazaki et al. | |
| 2011/0190584 A1 | 8/2011 | Sugahara | |
| 2011/0190710 A1 | 8/2011 | Miyoshi et al. | |
| 2011/0224494 A1 | 9/2011 | Piskun et al. | |
| 2011/0306833 A1 | 12/2011 | Saadat et al. | |
| 2012/0004577 A1 | 1/2012 | Saadat et al. | |
| 2012/0203066 A1 | 8/2012 | Okazaki et al. | |
| 2012/0226166 A1 | 9/2012 | Saadat et al. | |
| 2013/0023731 A1 | 1/2013 | Saadat et al. | |
| 2013/0131448 A1 | 5/2013 | Saadat et al. | |
| 2013/0274553 A1 | 10/2013 | Piskun et al. | |
| 2013/0345519 A1 | 12/2013 | Piskun et al. | |
| 2014/0276911 A1 * | 9/2014 | Smith ............... | A61B 17/32056 606/113 |
| 2014/0350412 A1 | 11/2014 | Saadat et al. | |
| 2015/0099931 A1 | 4/2015 | Leanna et al. | |
| 2016/0038721 A1 | 2/2016 | Lorenzo | |
| 2016/0095500 A1 | 4/2016 | Kumagai et al. | |
| 2016/0166314 A1 * | 6/2016 | Hancock ............ | A61B 18/1815 606/33 |
| 2016/0278757 A1 * | 9/2016 | Piskun ...................... | A61B 1/32 |
| 2017/0007279 A1 * | 1/2017 | Sharma .................. | A61B 18/14 |
| 2017/0014184 A1 * | 1/2017 | Hancock ............ | A61B 18/1492 |
| 2017/0079511 A1 | 3/2017 | Leanna et al. | |
| 2017/0105726 A1 * | 4/2017 | Smith ................ | A61B 17/0218 |
| 2017/0231647 A1 * | 8/2017 | Saunders ............. | A61B 17/221 606/113 |
| 2018/0110403 A1 | 4/2018 | Okazaki et al. | |

FOREIGN PATENT DOCUMENTS

| | | |
|---|---|---|
| EP | 1426072 A1 | 6/2004 |
| EP | 1426073 A1 | 6/2004 |
| EP | 2481336 A1 | 8/2012 |
| EP | 2481355 A1 | 8/2012 |
| EP | 2481377 A1 | 8/2012 |
| EP | 2481444 A1 | 8/2012 |
| EP | 2719346 A1 | 4/2014 |
| EP | 2982407 A2 | 2/2016 |
| EP | 3009062 A1 | 4/2016 |
| JP | H07-178113 A | 7/1995 |
| JP | H09-28666 A | 2/1997 |
| JP | H09-201367 A | 8/1997 |
| JP | H10-511589 A | 11/1998 |
| JP | 2001-517962 A | 10/2001 |
| JP | 2004-305714 A | 11/2004 |
| JP | 2009-531081 A | 9/2009 |
| JP | 2010-284503 A | 12/2010 |
| JP | 2011-509714 A | 3/2011 |
| JP | 2011-067600 A | 4/2011 |
| JP | 2012-161365 A | 8/2012 |
| JP | 2013-169422 A | 9/2013 |
| JP | 2013-183895 A | 9/2013 |
| JP | 2013-183933 A | 9/2013 |
| JP | 2014-239739 A | 12/2014 |
| JP | 2015-525109 A | 9/2015 |
| JP | 2016-36739 A | 3/2016 |
| JP | 2016-73401 A | 5/2016 |
| WO | WO 96/20749 A1 | 7/1996 |
| WO | WO 97/13451 A1 | 4/1997 |
| WO | 2004/089455 A2 | 10/2004 |
| WO | WO 2004/089456 A1 | 10/2004 |
| WO | WO 2007/109554 A2 | 9/2007 |
| WO | WO 2009/089530 A2 | 7/2009 |
| WO | WO 2011/084616 A2 | 7/2011 |
| WO | WO 2013/132861 A1 | 9/2013 |
| WO | WO 2013/192116 A1 | 12/2013 |
| WO | WO 2016/203606 A1 | 12/2016 |
| WO | WO 2017/090196 A1 | 6/2017 |

* cited by examiner

ENDOSCOPE DEVICE AND ENDOSCOPE SYSTEM WITH DEFORMING INSERTION PORTION WIRE

CROSS-REFERENCE TO RELATED APPLICATIONS

This is a continuation of International Application PCT/JP2016/065222, with an international filing date of May 23, 2016, which is hereby incorporated by reference herein in its entirety.

TECHNICAL FIELD

The present invention relates to an endoscope device and an endoscope system.

BACKGROUND ART

In the related art, there is a known method in which an endoscope is inserted into the pericardial cavity from below the xiphoid process, and the heart is observed and treated without performing a thoracotomy (for example, see U.S. Patent Application, Publication No. 2004/0064138, Specification).

CITATION LIST

Summary of Invention

An object of the present invention is to provide an endoscope device and an endoscope system with which it is possible to ensure a sufficient viewing field of an endoscope in the pericardial cavity.

A first aspect of the present invention is an endoscope device including: an elongated sheath having an endoscope insertion passage that penetrates therethrough in a longitudinal direction and into which an endoscope is inserted; and a wire that is provided in the sheath and that has a bending portion that bends toward the endoscope insertion passage, wherein the wire has a deforming region that is provided in a distal end portion of the sheath and that deforms between a normal form, in which the deforming region is disposed in the interior of the sheath or along an outer circumferential surface thereof, and a loop-shaped expanded form, in which the bending portion is bended and has a diameter larger than an outer diameter of the sheath.

In the abovementioned first aspect, the sheath may have a wire insertion passage that is formed along the longitudinal direction, that has an opening on a distal end surface of the sheath or on an outer circumferential surface in the vicinity of a distal end thereof, and into which the wire is inserted so as to move in the longitudinal direction, and the deforming region may be provided in a distal end portion of the wire inserted into the wire insertion passage.

In the abovementioned first aspect, the sheath may have two of the wire insertion passages, the wire may have two linear regions, which each include an end portion of the wire, and the deforming region, which is positioned between the two linear regions, and the two linear regions may be inserted into the two wire insertion passages so that the deforming region is positioned on the distal end side.

In the abovementioned first aspect, the expanded form may be such that the endoscope insertion passage is positioned substantially at the center thereof, when viewed in the longitudinal direction. In this case, the expanded form may have a circular shape or a polygonal shape.

In the abovementioned first aspect, the deforming region may have a loop portion that forms a loop shape in the expanded form, wherein the bending portion is provided farther on the base end side than the loop portion and that bends in a direction intersecting a plane defined by the loop-shaped loop portion in the expanded form.

In the abovementioned first aspect, a protrusion-amount controller that is provided on the base end side of the sheath, and is configured to control a protrusion amount of the deforming region from the wire insertion passages to a prescribed amount may be provided.

In the abovementioned first aspect, an outer sheath that accommodates the sheath so as to rotate about a longitudinal axis of the sheath may be provided, the distal end portion of the sheath may be protruded and exposed from a distal end of the outer sheath, the deforming region may be spirally wound around an outer circumferential surface of the distal end portion of the sheath, a distal end of the deforming region may be fixed to the sheath, and a base end of the deforming region may be fixed to the outer sheath.

A second aspect of the present invention is an endoscope system including: an endoscope having an elongated insertion portion that can be inserted into a body; and a wire that is provided in the insertion portion, wherein the wire has a deforming region that is provided in a distal end portion of the insertion portion and that is deformable between a normal form, in which the deforming region is disposed in the interior of the insertion portion or along an outer circumferential surface thereof, and a loop-shaped expanded form, which has a diameter larger than an outer diameter of the insertion portion.

DESCRIPTION OF EMBODIMENTS

First Embodiment

An endoscope system 100 according to a first embodiment of the present invention will be described below with reference to FIGS. 1A to 15.

Figure 1A:
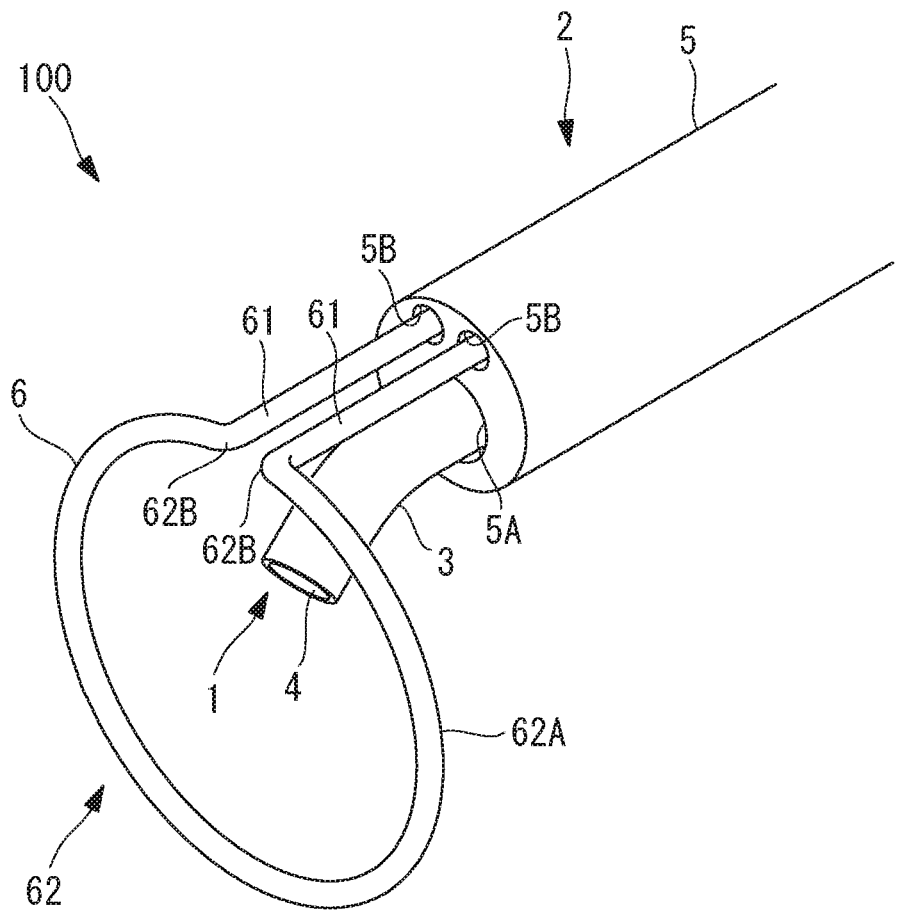
FIG. 1A is a perspective view showing the configuration of an endoscope device according to a first embodiment of the present invention and an endoscope system provided with the same.

As shown in FIG. 1A, the endoscope system 100 according to this embodiment is provided with: an endoscope 1; and an endoscope device 2 that is used by being attached to the outside of the endoscope 1.

The endoscope 1 is provided with: an elongated insertion portion 3 that has flexibility and that can be inserted into the pericardial cavity; and an objective optical system 4 that is provided in a distal end portion of the insertion portion 3 to observe a viewing field in front of the distal end of the insertion portion 3. The insertion portion 3 has, in the vicinity of the distal end thereof, a curved portion that has flexibility and with which the orientation of the distal end of the insertion portion 3 is changed in vertical and horizontal directions, when viewed from a longitudinal direction, by means of a bending mechanism (not shown).

The endoscope device 2 is provided with: an elongated sheath 5 that has flexibility and that can be inserted into the pericardial cavity; and a wire 6 that is provided in the sheath 5 in the longitudinal direction thereof.

The sheath 5 has: one endoscope insertion passage 5A into which the insertion portion 3 is inserted; and two wire insertion passages 5B into which the wire 6 is inserted. The three insertion passages 5A, 5B individually penetrate through the sheath 5 in the longitudinal direction thereof and have openings on the distal end surface and the base end surface of the sheath 5. The sheath 5 has a vertical direction and a horizontal direction that are orthogonal to the longitudinal direction thereof as well as orthogonal to each other. The two wire insertion passages 5B are positioned on the upper side of the endoscope insertion passage 5A and are provided side-by-side in the horizontal direction.

The wire 6 is formed of a shape memory material, such as nickel titanium, and has flexibility. The wire 6 has: two linear regions 61 that each include an end portion of the wire 6; and a deforming region 62 that is provided between the two linear regions 61 and that connects the two linear regions 61. The wire 6 is bent in half in the deforming region 62 so that the two linear regions 61 are substantially parallel to each other. The two linear regions 61 are respectively inserted into the wire insertion passages 5B from the distal end side of the sheath 5 to the base end side thereof, and at least a portion of the deforming region 62, which is disposed on the distal end side, protrudes from the wire insertion passages 5B.

The wire insertion passages 5B have inner diameters larger than the outer diameter of the wire 6, and the wire 6 can be moved in the wire insertion passages 5B in the longitudinal direction thereof. The two end portions of the wire 6 are pulled out from the base end of the sheath 5 and are disposed outside the sheath 5. Therefore, by pushing and pulling the two end portions of the wire 6 extending to the base end side of the sheath 5, the deforming region 62 can be advanced and retracted in the longitudinal direction of the sheath 5.

Figure 1B:
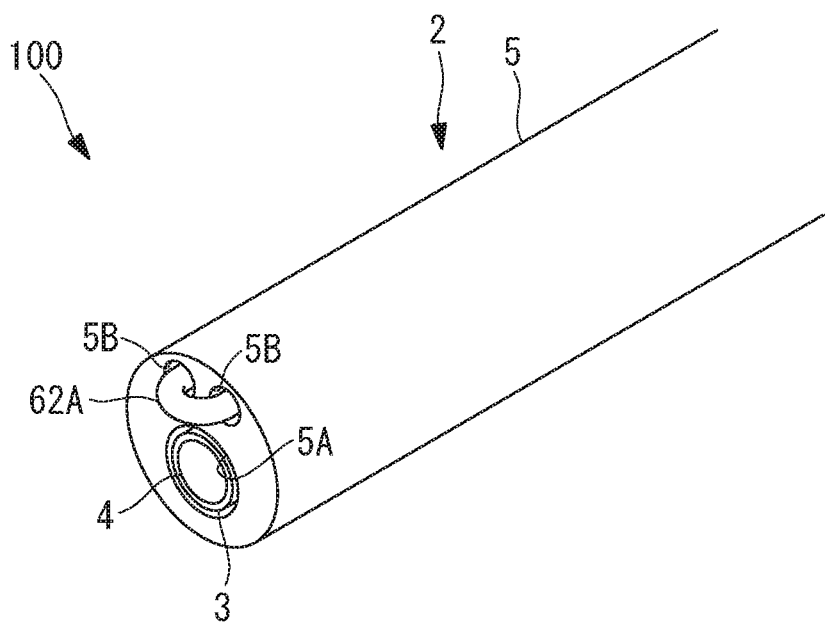
FIG. 1B is a perspective view showing the endoscope system in FIG. 1A when a wire is in a normal form.

The deforming region 62 is provided so as to be deformable between an expanded form shown in FIG. 1A and a normal form shown in FIG. 1B.

Specifically, the deforming region 62 has: a loop portion 62A; and two bending portions 62B that respectively connect end portions of the loop portion 62A to the distal ends of the linear regions 61. The loop portion 62A memorizes a loop shape in which the loop portion 62A is opened in between the two ends that are connected to the bending portions 62B. The two bending portions 62B memorize a shape in which the bending portions 62B are bent at substantially right angles in a direction intersecting a plane defined by the loop-shaped loop portion 62A. Therefore, the expanded form of the deforming region 62 has a loop shape expanding in a plane substantially perpendicular to the longitudinal direction of the sheath 5.

The deforming region 62 can be deformed from the expanded form to the normal form by means of the flexibility of the wire 6. In the normal form, most of the deforming region 62 is disposed in the wire insertion passages 5B, and only a portion of the deforming region 62 protrudes from the wire insertion passages 5B. Therefore, in the normal form, the bending portions 62B have a substantially linear shape, in which the bending portions 62B extend along extension lines of the linear regions 61, and the loop portion 62A has a U shape.

The deforming region 62 generates a restoring force for restoring the deforming region 62 from the normal form to the expanded form, for example, by being warmed up to body temperature. Therefore, in a state in which at least the distal end portion of the sheath 5 is disposed inside the body, by pushing the two end portions of the wire 6 to the distal end side and making the entire deforming region 62 protrude from inside the wire insertion passages 5B, the deforming region 62 is made to self-deform from the normal form into the expanded form. By pulling the two end portions of the wire 6 after the deforming region 62 has deformed into the expanded form, the deforming region 62 becomes accommodated in the wire insertion passages 5B while deforming into the normal form.

The loop portion 62A in the expanded form has an outer diameter larger than the outer diameter of the sheath 5, and protrudes farther radially outward than the outer circumferential surface of the sheath 5. Therefore, the loop portion 62A expands in the horizontal direction of the sheath 5 due to the deformation from the normal form into the expanded form. The bending portions 62B in the expanded form bend toward the same side as the endoscope insertion passage 5A (lower side of the sheath 5), whereby the loop portion 62A in the expanded form also protrudes farther downward than the outer circumferential surface of the sheath 5.

Next, the operation of the thus-configured endoscope system 100 will be described.

To observe the heart A by using the endoscope system 100 according to this embodiment, an operator pulls the two end portions of the wire 6 to place the deforming region 62 in the normal form, inserts the sheath 5 in this state into the body from below the xiphoid process, and places the sheath 5 into the interior of the pericardial cavity from below the xiphoid process. Next, the operator inserts the insertion portion 3 of the endoscope 1 into the pericardial cavity via the endoscope insertion passage 5A, and places the distal end of the insertion portion 3 in the vicinity of the distal end of the sheath 5.

Figure 2A:
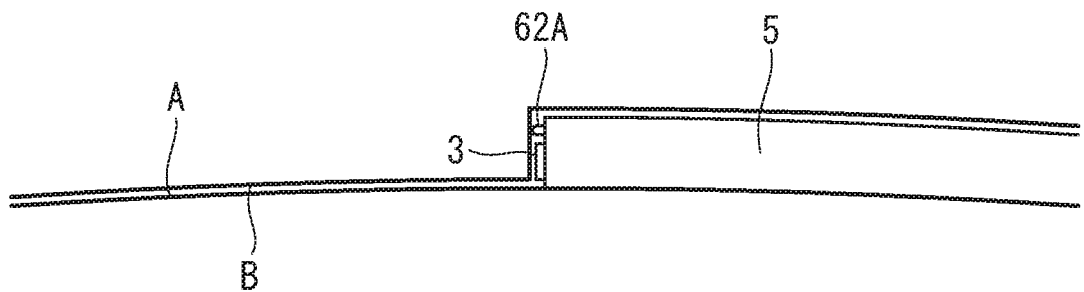
FIG. 2A is a diagram showing an operating state of the endoscope system in FIG. 1A.

At this time, as shown in FIG. 2A, because the pericardium B is in close contact with the outer surface of the heart A, there is almost no space in the periphery of the distal end of the sheath 5, and it is not possible to observe the interior of the pericardial cavity with the endoscope 1. Therefore, the position of the insertion portion 3 in the pericardial cavity is checked by using an ultrasonic imaging device, an X-ray fluoroscopy apparatus or the like, and the distal end of the insertion portion 3 is placed at a desired position.

Figure 2B:
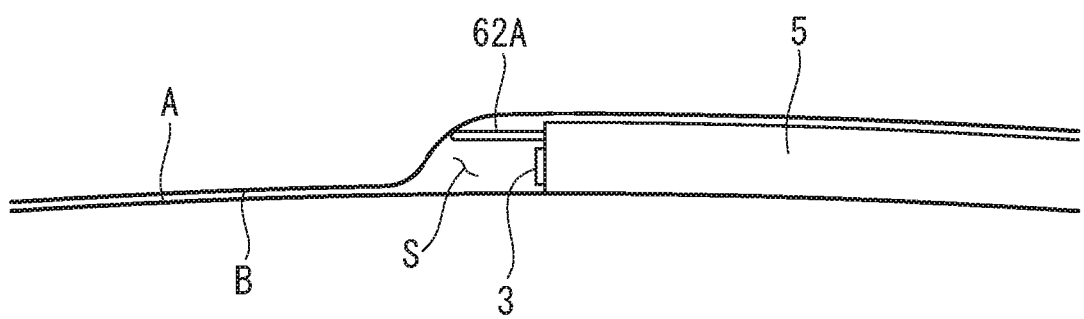
FIG. 2B is a diagram showing an operating state of the endoscope system in FIG. 1A.

Next, the operator pushes the two end portions of the wire 6, which are disposed on the base end side of the sheath 5, to the distal end side, thereby making the deforming region 62 protrude from inside the wire insertion passages 5B. In the process in which the deforming region 62 protrudes from inside the wire insertion passages 5B, first, as shown in FIG. 2B, the loop portion 62A protrudes from inside the wire insertion passages 5B, and the loop portion 62A expands into a loop shape in a plane substantially parallel to the longitudinal direction of the sheath 5.

When the sheath 5 is placed in such a manner that the lower side of the sheath 5 faces the heart A side, the expanded loop portion 62A holds the pericardium B at a position farther away from the outer surface of the heart A than the endoscope insertion passage 5A is, and a space S is formed in front of the distal ends of the sheath 5 and the insertion portion 3. Therefore, in this state (first state), it is possible to observe the area in front of the distal end of the sheath 5 with the endoscope 1.

Figure 2C:
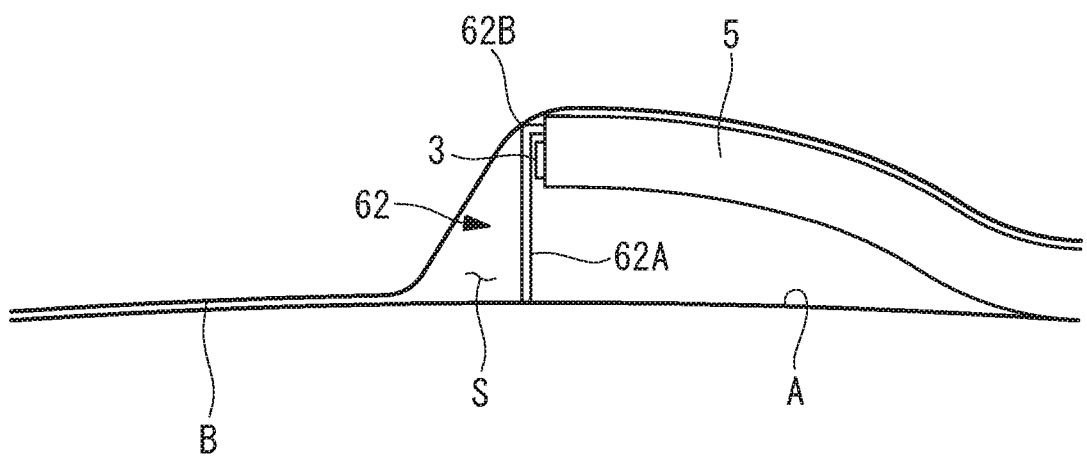
FIG. 2C is a diagram showing an operating state of the endoscope system in FIG. 1A.

When the operator further pushes the two end portions of the wire 6 to make the bending portions 62B protrude from inside the wire insertion passages 5B, as shown in FIG. 2C, the bending portions 62B undergo bending deformations, whereby the loop-shaped loop portion 62A is placed substantially perpendicularly to the outer surface of the heart A. Then, the loop portion 62A protruding farther downward (toward the heart A) than the sheath 5 lifts the sheath 5 in a direction in which the sheath 5 is separated from the outer surface of the heart A, and the outer circumferential surface of the sheath 5 holds the pericardium B at a position further separated from the outer surface of the heart A.

At this time, the distance between the outer surface of the heart A and the inner surface of the pericardium B becomes larger than the outer diameter of the sheath 5. Therefore, in this state (second state), a space S that is larger than that in the first state is formed in front of the distal ends of the sheath 5 and the insertion portion 3, and it is possible to observe a larger area in front of the distal end of the sheath 5 with the endoscope 1. Because the insertion portion 3 is disposed at a position separated from the outer surface of the heart A, it is possible to observe the outer surface of the heart A from an overhead view by bending the curved portion provided in the distal end portion of the insertion portion 3 toward the heart A.

Figure 2D:
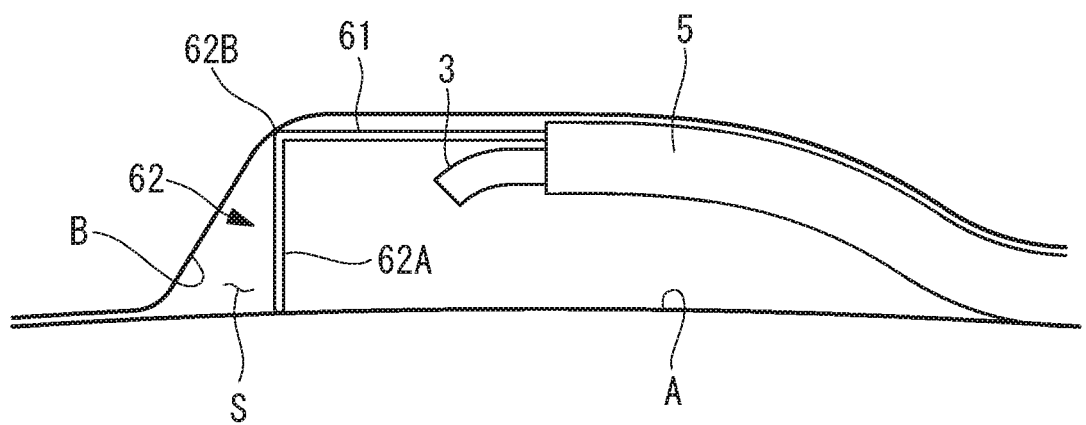
FIG. 2D is a diagram showing an operating state of the endoscope system in FIG. 1A.

From the second state shown in FIG. 2C, when the operator further pushes the two end portions of the wire 6 to increase the protrusion amount of the deforming region 62 from the wire insertion passages 5B, as shown in FIG. 2D, the space S expands in front of the distal end of the sheath 5. By doing so, it is possible to observe, with the endoscope 1, not only the vicinity of the distal end of the sheath 5 but also a position separated from the distal end of the sheath 5.

As described above, according to this embodiment, there is an advantage in that, with a simple operation in which the wire 6 is merely pushed into the wire insertion passages 5B, it is possible to form a space S in the periphery of the distal end of the sheath 5 disposed in the pericardial cavity, and to ensure a sufficient viewing field of the endoscope 1. In the second state, there is an advantage in that it is possible to observe the outer surface of the heart A from an overhead view by holding the distal end portion of the sheath 5, by means of the expanded deforming region 62, at a position separated from the outer surface of the heart A. There is an advantage in that it is possible to adjust the range of the viewing field by changing the size of the space S in a direction along the longitudinal direction of the sheath 5 in accordance with the protrusion amount of the wire 6 from the distal end surface of the sheath 5.

Figure 3:
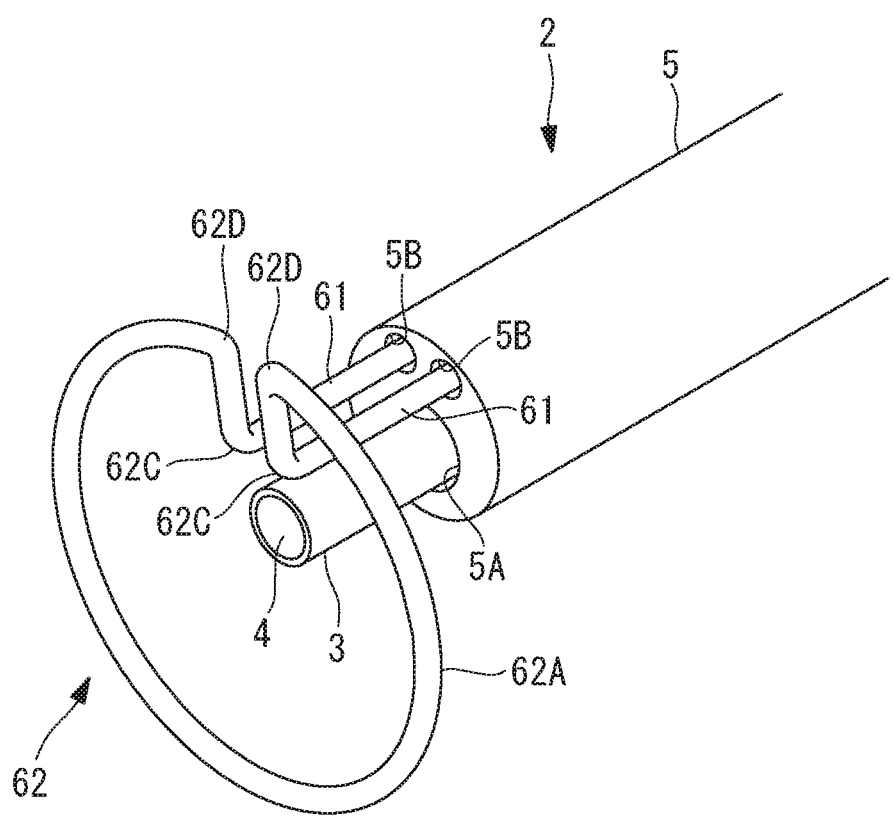
FIG. 3 is a diagram showing a modification of the endoscope device in FIG. 1A.
Figure 4:
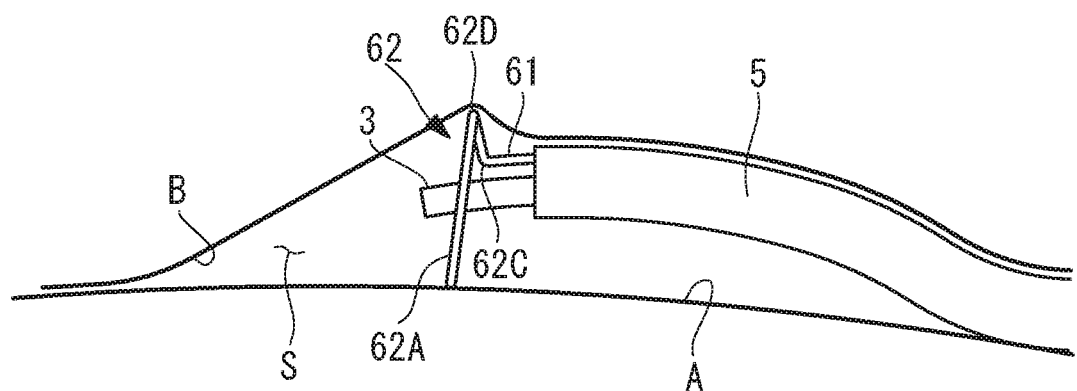
FIG. 4 is a diagram showing an operating state of the endoscope device in FIG. 3.

Although the loop portion 62A in the expanded form protrudes toward the left and right sides and the lower side of the sheath 5 in this embodiment, as shown in FIG. 3, the loop portion 62A may be configured so as to also protrude toward the upper side of the sheath 5 by providing a plurality of bending portions 62C, 62D along the longitudinal direction thereof. By doing so, as shown in FIG. 4, a space S is formed not only on the heart A side of the sheath 5 but also on the pericardium B side thereof by means of the loop portion 62A. Therefore, it is possible to observe the pericardium B and tissue (for example, the lung or phrenic nerve) that is positioned outside the pericardium B by bending the curved portion of the insertion portion 3 toward the pericardium B.

In the modification shown in FIG. 3, the deforming region 62 has: the loop portion 62A; two first bending portions 62C that are adjacent to the distal ends of the linear regions 61; and two second bending portions 62D that are provided between the first bending portions 62C and the loop portion 62A. In the expanded form, the first bending portions 62C bend at substantially right angles toward the upper side of the sheath 5, and the two second bending portions 62D respectively bend at substantially right angles toward the left and right sides of the sheath 5. The loop portion 62A in the expanded form has a substantially circular shape in which the endoscope insertion passage 5A is positioned substantially at the center of the loop portion 62A, when the endoscope device 2 is viewed in the longitudinal direction thereof. The loop portion 62A may have a polygonal shape instead of the circular shape.

When the sheath 5 is rotated about the longitudinal axis thereof in a state in which the deforming region 62 has reached the expanded form, the loop portion 62A rotates about the longitudinal axis of the sheath 5 while the space S remains in front of the distal end of the sheath 5 as well as on the lateral sides thereof, and the insertion portion 3 in the endoscope insertion passage 5A also rotates. Therefore, by rotating the sheath 5 in a state in which the curved portion of the insertion portion 3 is bent, it is possible to observe the interior of the pericardial cavity from various directions.

Figure 5:
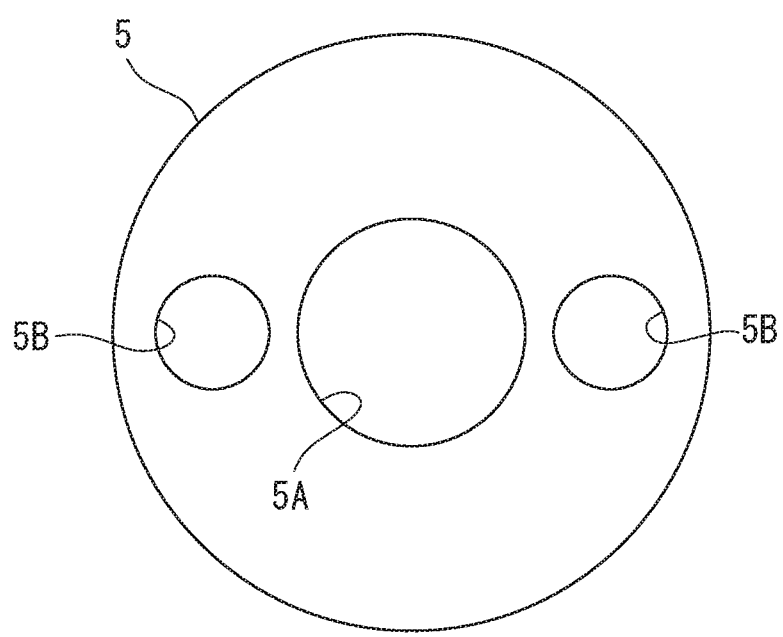
FIG. 5 is a diagram showing another modification of the endoscope device in FIG. 1A.

Although the two wire insertion passages 5B are provided on the same side as the endoscope insertion passage 5A in this embodiment, alternatively, as shown in FIG. 5, the two wire insertion passages 5B may be provided on both sides of the endoscope insertion passage 5A so that the two wire insertion passages 5B and the endoscope insertion passage 5A are arranged in a row in a radial direction of the sheath 5.

In the case in which the two wire insertion passages 5B are provided on the same side as the endoscope insertion passage 5A, as shown in FIGS. 1A to 4, when the curved portion of the insertion portion 3 is bent toward the wire insertion passages 5B, there is a possibility that the insertion portion 3 comes into contact with the wire 6 protruding from the wire insertion passages 5B. In the process of assembling the endoscope device 2, it is necessary to determine the relative orientations of the sheath 5 and the wire 6 so that the bending portions 62B bend toward the endoscope insertion passage 5A.

In contrast, with this modification, it is possible to prevent the wire 6 from interfering with the movable range of the curved portion, which bends in the vertical direction. Because it is not necessary to determine the relative orientations of the wire 6 and the sheath 5, it is possible to facilitate assembly of the endoscope device 2. {0036}

Although the two wire insertion passages 5B are provided in this embodiment, alternatively, only one wire insertion passage 5B may be provided, and the two linear regions 61 may be inserted into the same wire insertion passage 5B.

Although the deforming region 62 in the expanded form has a circular loop shape expanding in a plane substantially perpendicular to the longitudinal direction of the sheath 5 in this embodiment, the expanded form of the deforming region 62 is not limited thereto. FIGS. 6 to 10B show modifications of the expanded form of the deforming region 62.

Figure 6:
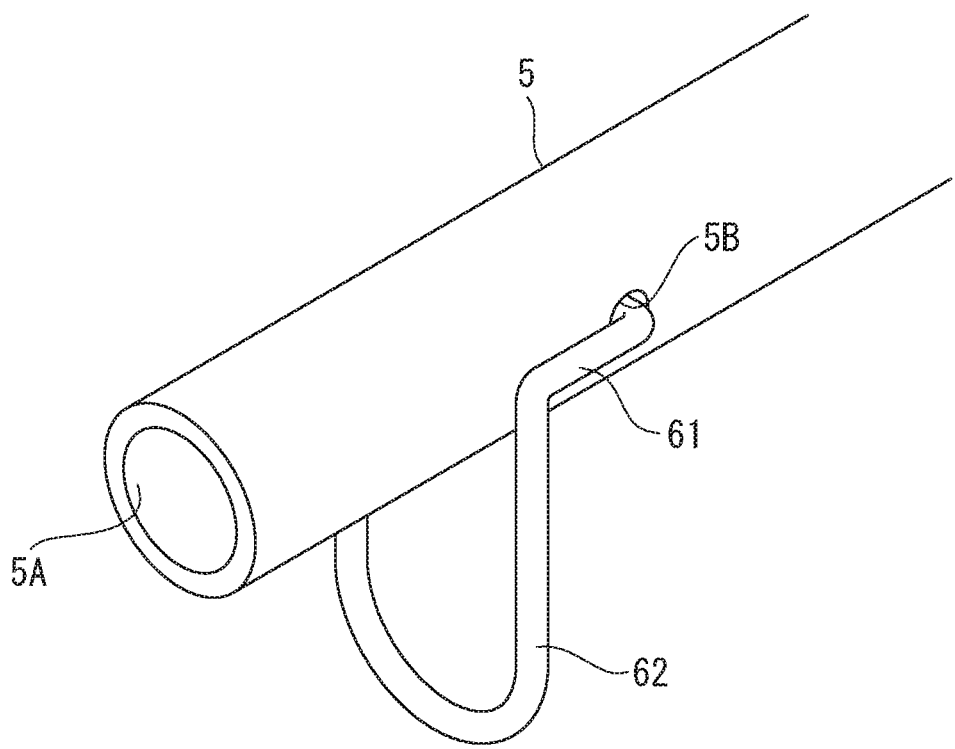
FIG. 6 is a diagram showing another modification of the endoscope device in FIG. 1A.

As shown in FIG. 6, the wire insertion passages 5B may have openings on the outer circumferential surface in the vicinity of the distal end of the sheath 5, and the expanded form of the deforming region 62 may have a U-shaped loop expanding in a plane substantially perpendicular to the longitudinal direction of the sheath 5.

Figure 7:
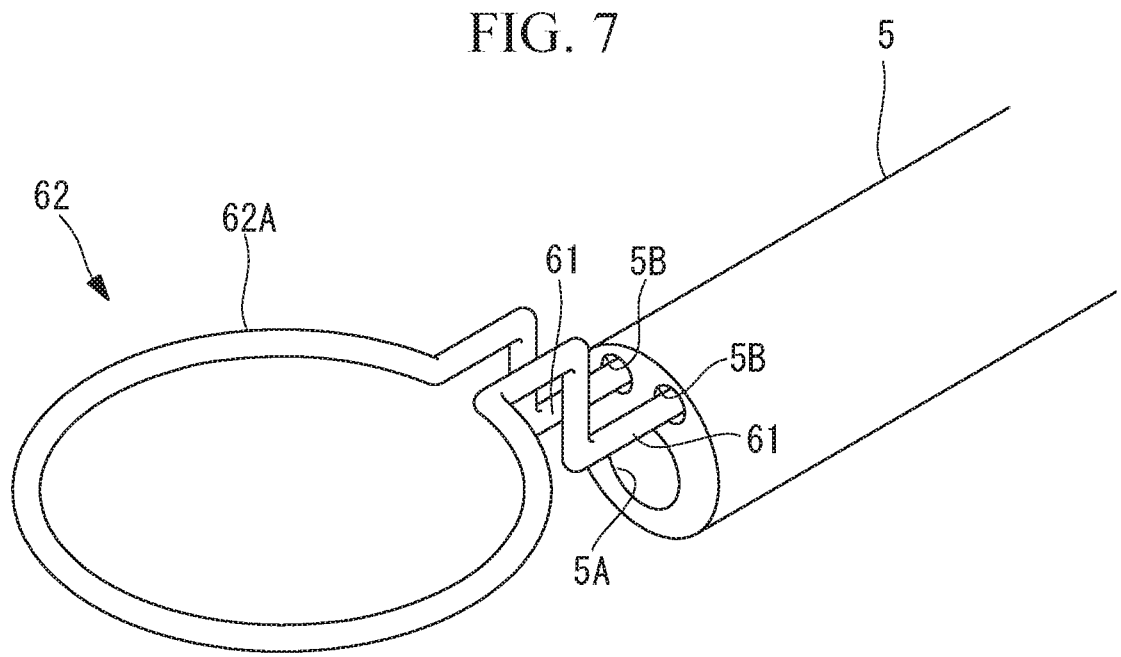
FIG. 7 is a diagram showing another modification of the endoscope device in FIG. 1A.

The deforming region 62 in FIG. 7 is a modification of the deforming region 62 in FIG. 3. As shown in FIG. 7, the expanded form of the loop portion 62A may have a loop shape expanding in a plane parallel to the longitudinal direction of the sheath 5.

Figure 8:
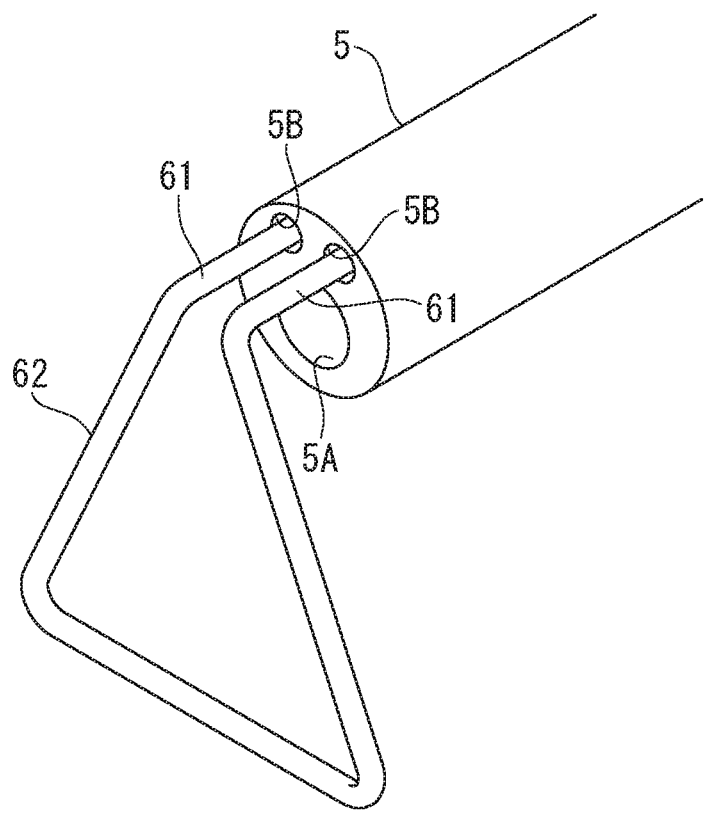
FIG. 8 is a diagram showing another modification of the endoscope device in FIG. 1A.

As shown in FIG. 8, the expanded form of the loop portion 62A may have a polygonal shape (triangular in an example shown in FIG. 8) instead of the circular shape. By forming a portion of the loop portion 62A, which comes into contact with the outer surface of the heart A, in a straight-line shape, it is possible to increase the contact area between the heart A and the loop portion 62A, and to support the pericardium B and the sheath 5, by means of the loop portion 62A, in a more stable manner.

Figure 9:
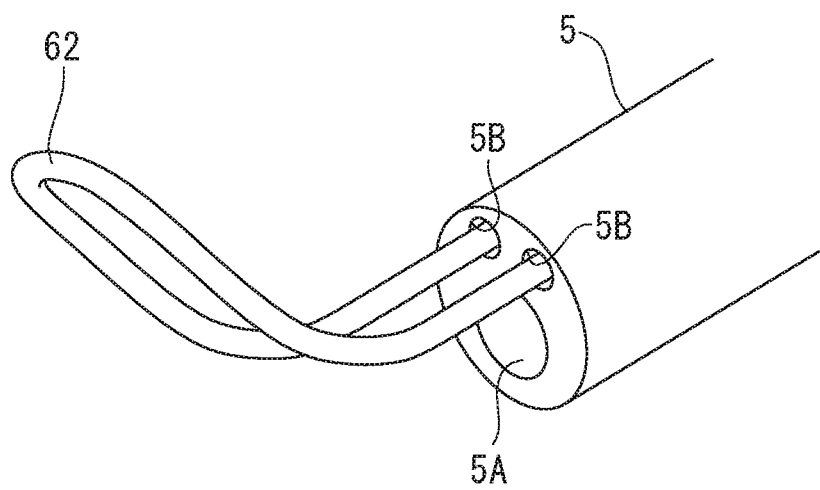
FIG. 9 is a diagram showing another modification of the endoscope device in FIG. 1A.
Figure 10A:
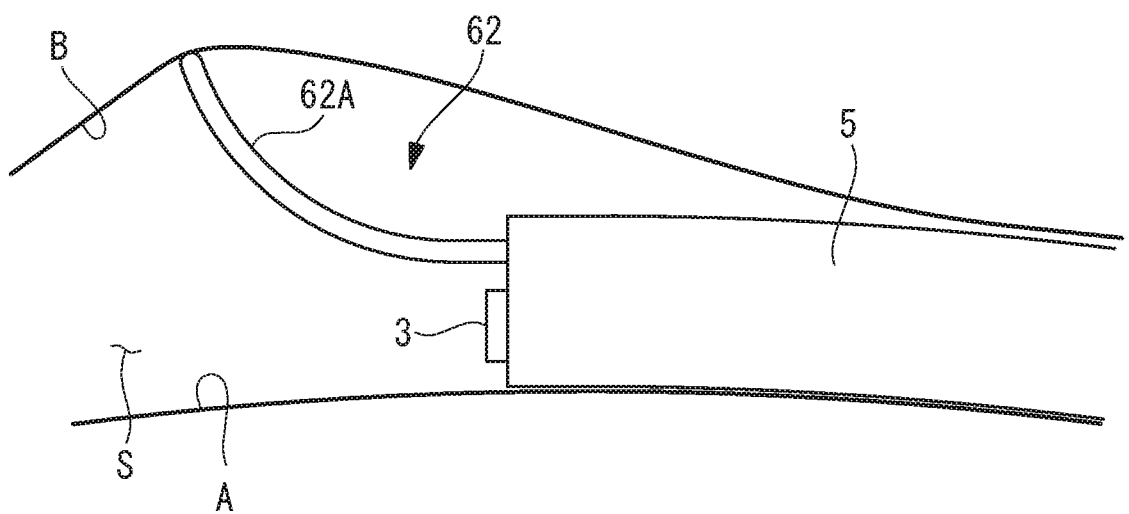
FIG. 10A is a diagram showing an operating state of the endoscope device in FIG. 9.
Figure 10B:
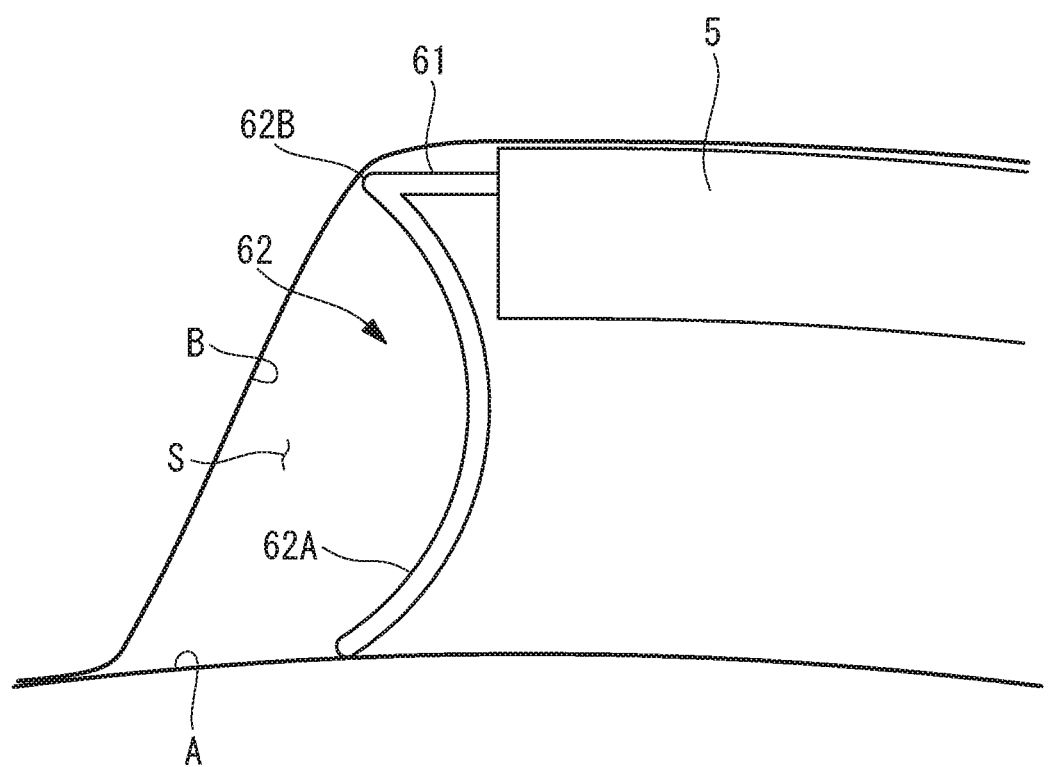
FIG. 10B is a diagram showing an operating state of the endoscope device in FIG. 9.

As shown in FIG. 9, the expanded form of the loop portion 62A may have a shape in which the loop portion 62A is bent outward in a radial direction of the sheath 5. By doing so, as shown in FIG. 10A, it is possible to hold the pericardium B at a position more separated from the outer surface of the heart A, as compared to the first state shown in FIG. 2B. FIG. 10B shows the second state in which the bending portions 62B protrude from the wire insertion passages 5B.

Although the wire 6 is bent in half and the deforming region 62 is provided at an intermediate position in the longitudinal direction of the wire 6 in this embodiment, alternatively, as shown in FIGS. 11 to 14, the deforming region 62 may be provided in a distal end portion of the wire 6. In this case, the wire 6 has a single linear region 61 including the base end thereof.

Figure 11:
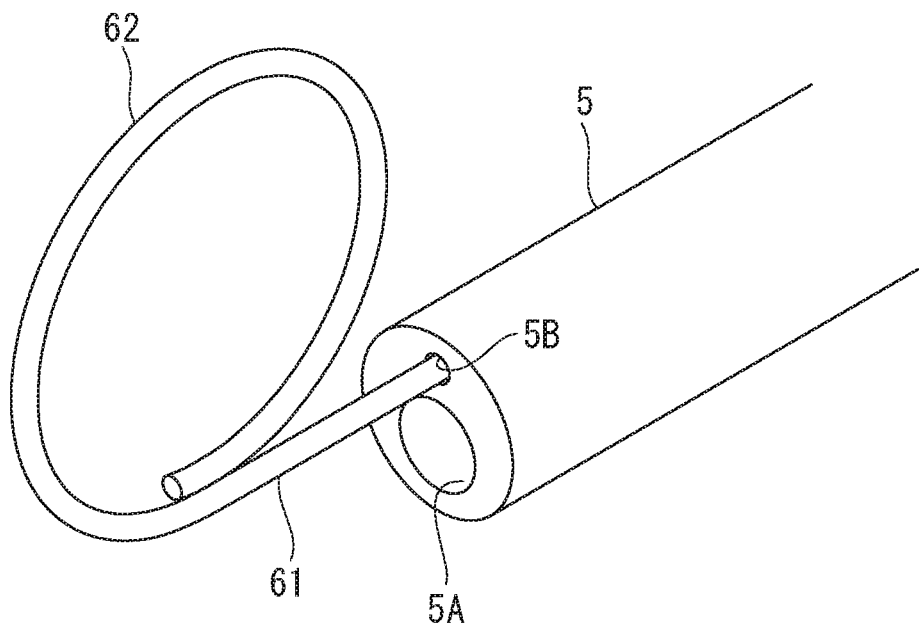
FIG. 11 is a diagram showing another modification of the endoscope device in FIG. 1A.
Figure 12:
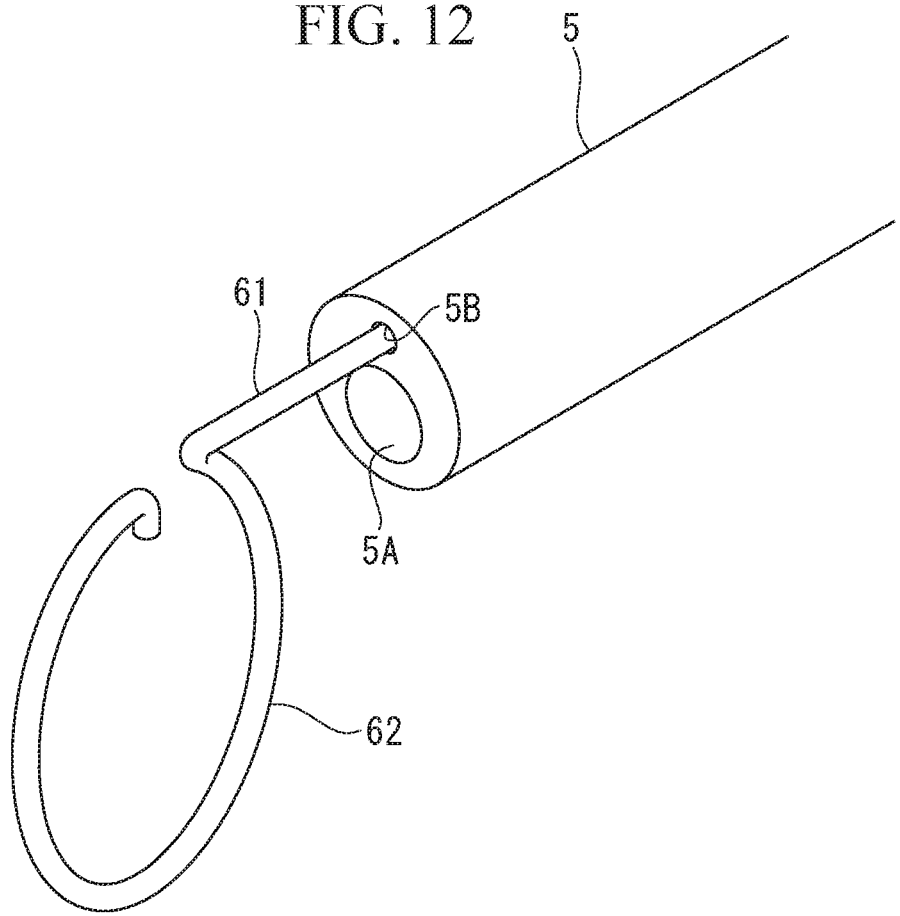
FIG. 12 is a diagram showing another modification of the endoscope device in FIG. 1A.

The expanded form of the deforming region 62 may have a circular loop shape expanding in a plane substantially parallel to the longitudinal direction of the sheath 5, as shown in FIG. 11, or a circular loop shape expanding in a plane substantially perpendicular to the longitudinal direction of the sheath 5, as shown in FIG. 12.

Figure 13:
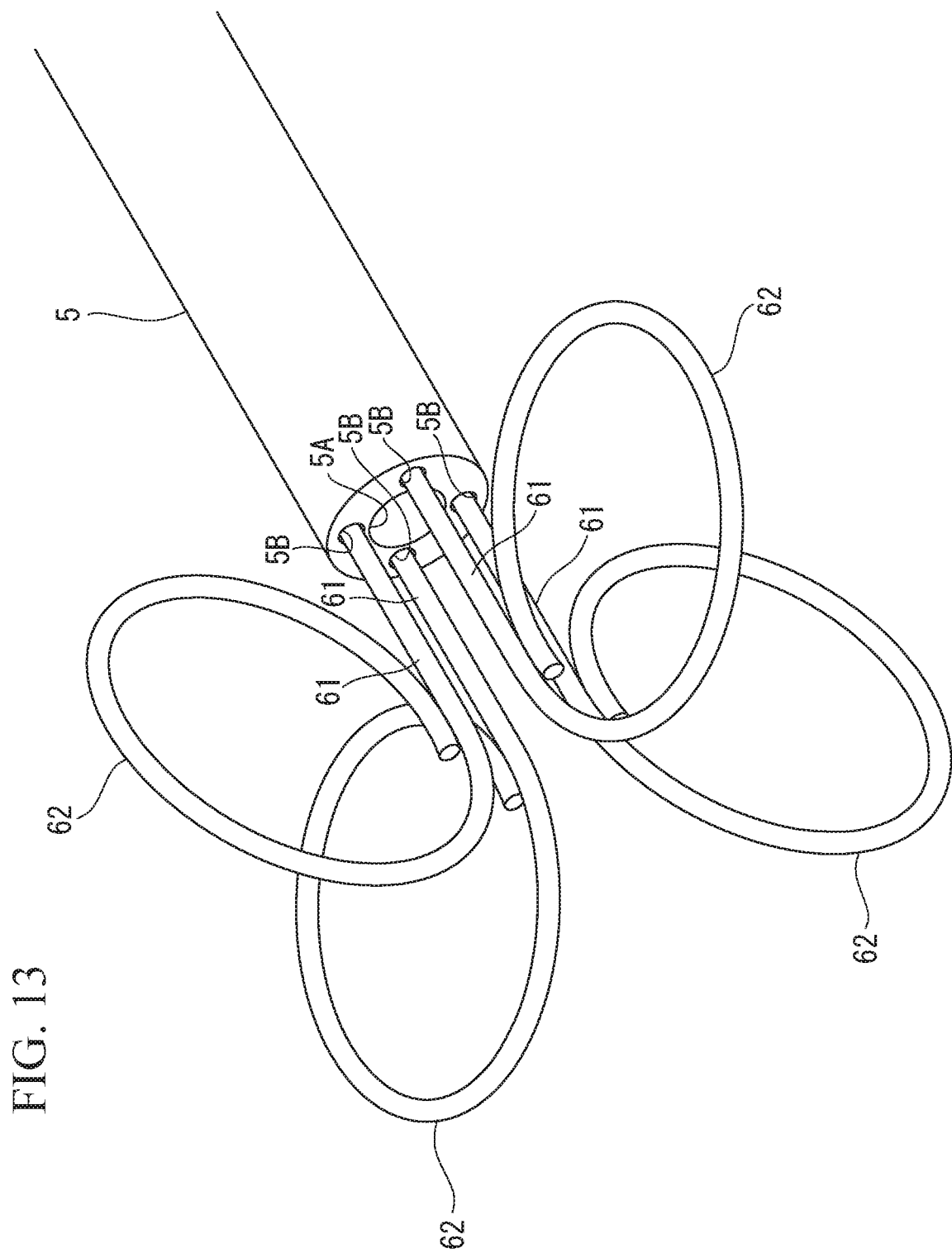
FIG. 13 is a diagram showing another modification of the endoscope device in FIG. 1A.

In a modification shown in FIG. 13, the sheath 5 has a plurality of wire insertion passages 5B, and a plurality of wires 6 are inserted into the respective wire insertion passages 5B. In this case, it is preferable that the orientations of the plurality of wires 6 be adjusted so that the deforming regions 62 of the plurality of wires 6 protrude in different directions from one another. With this modification, because the individual wires 6 can be independently advanced and retracted, it is possible to form spaces only on desired sides of the sheath 5, from among the upper, lower, left, and right sides.

Figure 14:
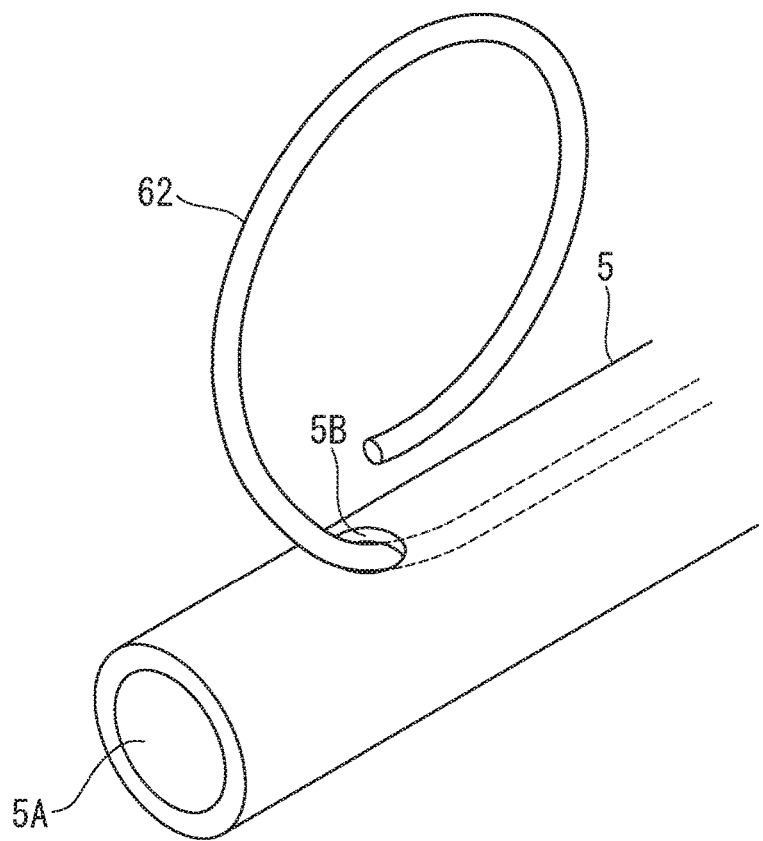
FIG. 14 is a diagram showing another modification of the endoscope device in FIG. 1A.

As shown in FIG. 14, the wire insertion passage 5B may be configured such that the wire insertion passage 5B has an opening on the outer circumferential surface of the sheath 5, instead of the distal end surface of the sheath 5, and that the deforming region 62 is projected and retracted through the opening on the outer circumferential surface of the sheath 5.

In this embodiment, a protrusion-amount control portion for controlling the protrusion amount of the deforming region 62 from the wire insertion passages 5B may be provided.

Figure 15:
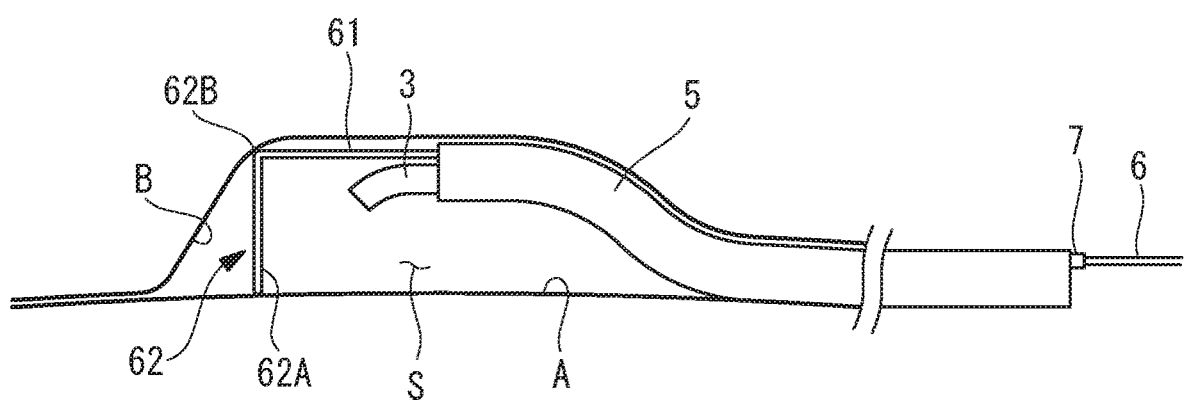
FIG. 15 is a diagram showing an operating state of another modification of the endoscope device in FIG. 1A.

The protrusion-amount control portion (protrusion-amount controller) 7 is, for example, as shown in FIG. 15, a marker that is provided on each of the two end portions of the wire 6.

The markers 7 are provided on the wire 6, at positions coincident with a prescribed position of the sheath 5 (for example, the base end of the sheath 5) when the protrusion amount of the deforming region 62 reaches a prescribed amount.

By doing so, the operator can place the deforming region 62 at an appropriate position by pushing the wire 6 until the markers 7 are disposed at the prescribed positions.

Second Embodiment

Next, an endoscope system 200 according to a second embodiment of the present invention will be described with reference to FIGS. 16 and 17.

In the description of this embodiment, components that are different from those of the first embodiment will be mainly described, and components that are the same as those of the first embodiment will be assigned the same reference signs, and descriptions thereof will be omitted.

Figure 16:
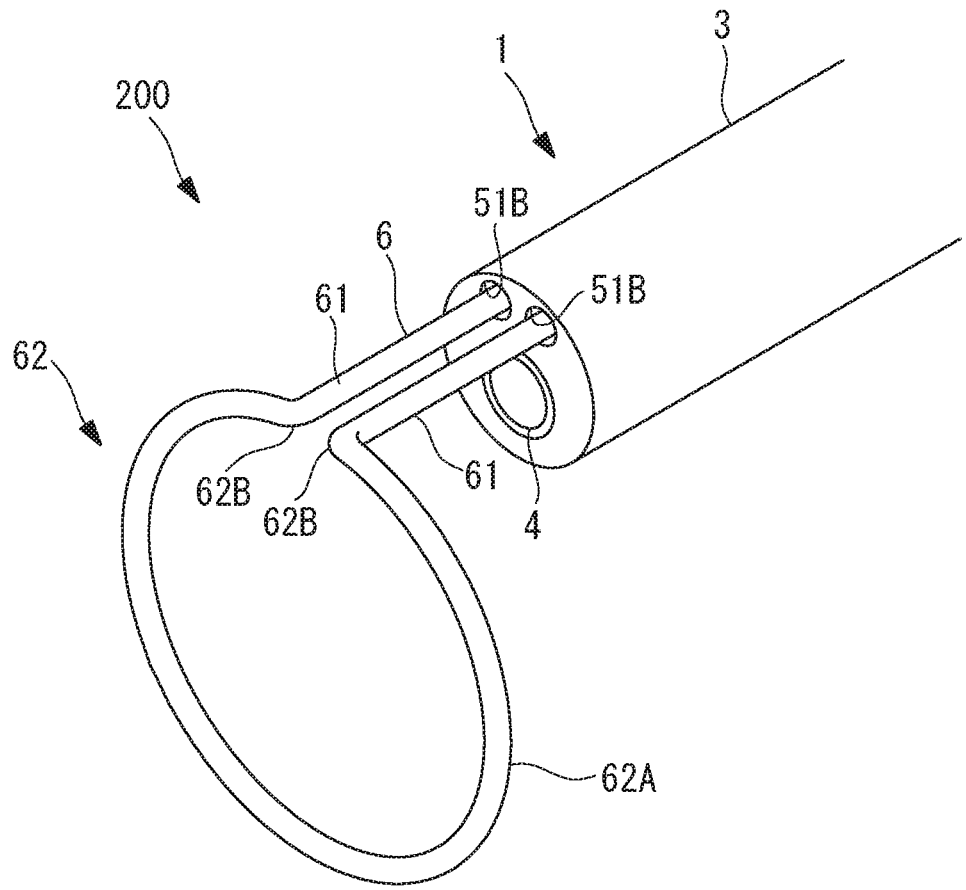
FIG. 16 is a perspective view showing the configuration of an endoscope system according to a second embodiment of the present invention.

As shown in FIG. 16, the endoscope system 200 according to this embodiment is not provided with a sheath 5, and a wire 6 is provided in an insertion portion 3 of an endoscope 1.

As with the sheath 5 in the first embodiment, the insertion portion 3 has two wire insertion passages 51B into which the wire 6 is inserted. The two insertion passages 51B individually penetrate through the insertion portion 3 in the longitudinal direction thereof and have openings on the distal end surface and the base end surface of the insertion portion 3. The insertion portion 3 has a vertical direction and a horizontal direction that are orthogonal to the longitudinal direction thereof as well as orthogonal to each other. The two wire insertion passages 51B are positioned on the upper side of an objective optical system 4 and provided side-by-side in the horizontal direction.

The wire insertion passages 51B have inner diameters larger than the outer diameter of the wire 6, and the wire 6 can be moved in the wire insertion passages 51B in the longitudinal direction thereof. Two end portions of the wire 6 are pulled out from a port (not shown), which is provided in an operation portion (not shown) connected to the base end of the insertion portion 3, and are disposed outside the endoscope 1. Therefore, by pushing and pulling the two end portions of the wire 6 extending to the base end side of the insertion portion 3, a deforming region 62 is moved in the longitudinal direction of the insertion portion 3.

The configuration of the wire 6 in this embodiment is the same as the configuration of the wire 6 shown in FIGS. 1A and 1B.

According to this embodiment, there is an advantage in that it is possible to achieve a structure with a smaller diameter, as compared to the first embodiment, by eliminating the sheath 5 disposed on the outer side of the insertion portion 3. Because the other effects of this embodiment are the same as those of the first embodiment, descriptions thereof will be omitted.

In this embodiment, the modifications shown in FIGS. 3 to 14, described in the first embodiment, may be applied as appropriate.

Figure 17:
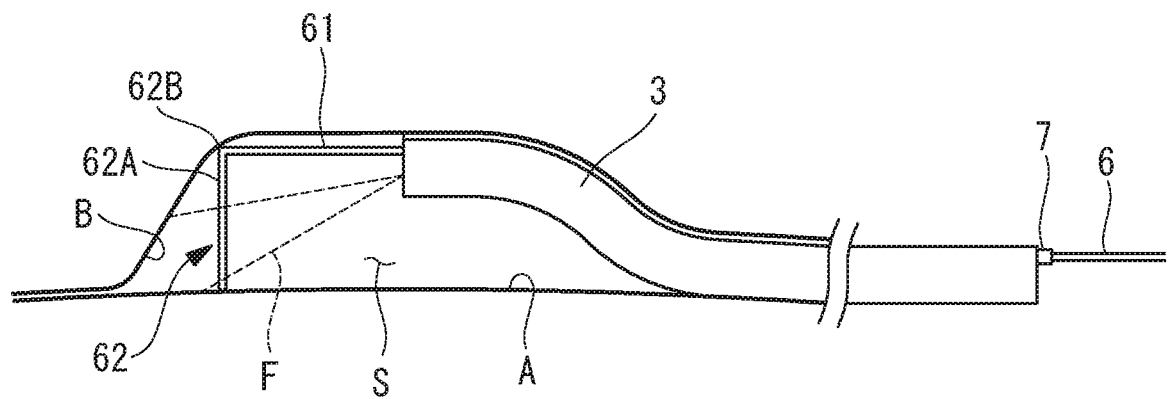
FIG. 17 is a diagram showing an operating state of a modification of the endoscope system in FIG. 16.

In this embodiment also, as shown in FIG. 17, it is preferable that a protrusion-amount control portion 7 for controlling the protrusion amount of the deforming region 62 from the wire insertion passages 51B be provided. In this embodiment, markers 7 are provided on the wire 6, at positions coincident with a prescribed position of the endoscope 1 (for example, the port from which a base end portion of the wire 6 is pulled out) when the protrusion amount of the deforming region 62 reaches the maximum, among the protrusion amounts by which the entire deforming region 62 in the expanded form is positioned outside a viewing field F of the endoscope 1.

By doing so, the operator can place the deforming region 62 at a position at which the deforming region 62 does not enter the viewing field F of the endoscope 1 and also at which a space S becomes largest, by pushing the wire 6 until the markers 7 are disposed at the prescribed positions.

Third Embodiment

Next, an endoscope system 300 according to a third embodiment of the present invention will be described with reference to FIGS. 18 to 20B.

In the description of this embodiment, components that are different from those of the first embodiment will be mainly described, and components that are the same as those of the first embodiment will be assigned the same reference signs, and descriptions thereof will be omitted.

Figure 18:
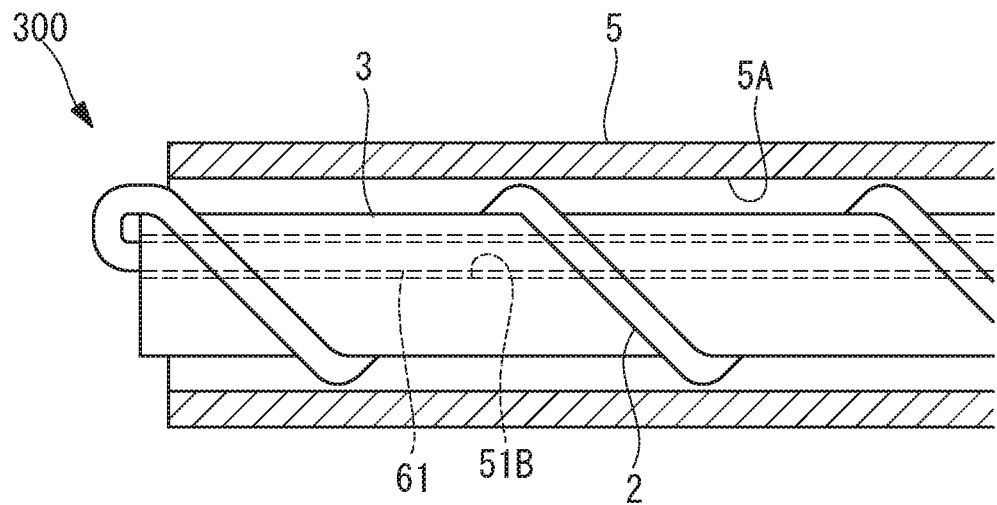
FIG. 18 is a cross-sectional view showing the configuration of an endoscope system according to a third embodiment of the present invention.
Figure 19:
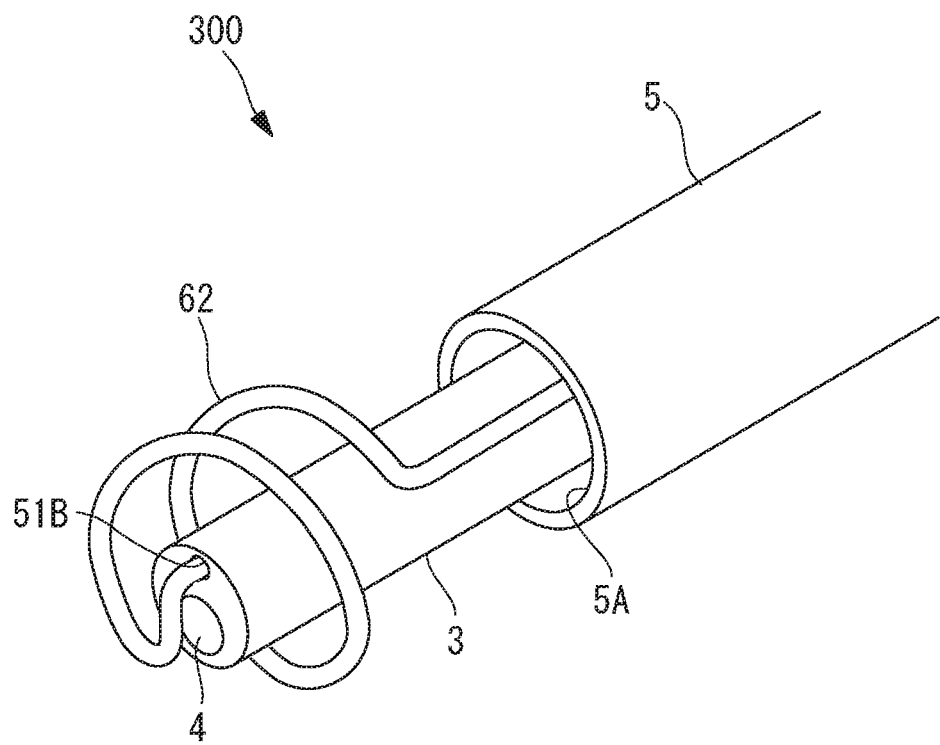
FIG. 19 is a perspective view showing the endoscope system in FIG. 18 when a wire is in an expanded form.

As shown in FIGS. 18 and 19, the endoscope system 300 according to this embodiment differs from that in the first embodiment in the arrangement and form of a wire 6.

An insertion portion 3 of an endoscope 1 has only one wire insertion passage 51B, which has been described in the second embodiment.

An endoscope insertion passage 5A of a sheath 5 has an inner diameter larger than the outer diameter of the insertion portion 3, and the difference between the inner diameter of the endoscope insertion passage 5A and the outer diameter of the insertion portion 3 is larger than twice the diameter of the wire 6.

The wire 6 is the same as the wire 6 in the first embodiment in that the wire 6 has two linear regions 61 that each include an end portion of the wire 6, and a deforming region 62 that is provided between the two linear regions 61 and that connects the two linear regions 61. However, in this embodiment, one of the linear regions 61 is inserted into the wire insertion passage 51B from the distal end side of the insertion portion 3 to the base end side thereof, and the other linear region 61 is inserted, from the distal end side of the sheath 5 to the base end side thereof, into a cylindrical gap formed between the outer circumferential surface of the insertion portion 3 and the inner circumferential surface of the endoscope insertion passage 5A of the sheath 5.

The deforming region 62 memorizes a spiral loop shape that has an outer diameter larger than the outer diameter of the sheath 5, and that has a certain pitch in the longitudinal direction of the insertion portion 3. When the two end portions of the wire 6 are pulled, the deforming region 62 deforms into a spiral-shaped normal form, in which the deforming region 62 comes into close contact with the outer circumferential surface of the insertion portion 3 and winds around said outer circumferential surface. In this state, as shown in FIG. 18, it is possible to accommodate the deforming region 62 in the endoscope insertion passage 5A of the sheath 5. When the two end portions of the wire 6 are pushed to the distal end side, or when the sheath 5 is pulled to the base end side with respect to the insertion portion 3, thus making the distal end portion of the insertion portion 3 protrude from inside the endoscope insertion passage 5A, the deforming region 62 deforms into a spiral-shaped expanded form having a larger diameter, with the insertion portion 3 substantially at the center.

In this embodiment, the operator can cause deformation of the deforming region 62, which is wound around the outer circumferential surface of the insertion portion 3, from the normal form into the expanded form by pulling the sheath 5 to the base end side with respect to the insertion portion 3 or by pushing the two end portions of the wire 6 into the insertion passages 5A, 51B.

In this case, because the deforming region 62 in the expanded form protrudes toward both the lower side and the upper side of the insertion portion 3, there is an advantage in that it is possible to form spaces both on the heart A side and on the pericardium B side of the insertion portion 3. Because the deforming region 62 in the expanded form also expands in the longitudinal direction of the insertion portion 3, there is an advantage in that it is possible to form a large space also in the longitudinal direction of the insertion portion 3. Because the normal form has a shape similar to that of the expanded form, there is an advantage in that it is possible to stably maintain the spiral loop shape memorized in the deforming region 62.

Figure 20A:
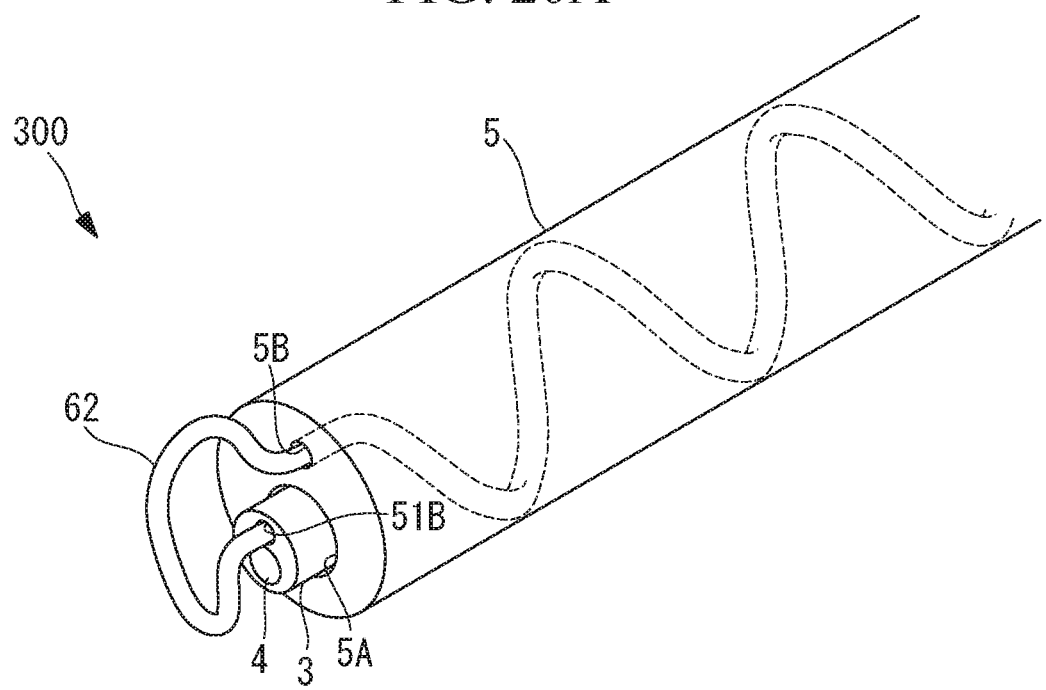
FIG. 20A is a perspective view showing the configuration of a modification of the endoscope system in FIG. 18.
Figure 20B:
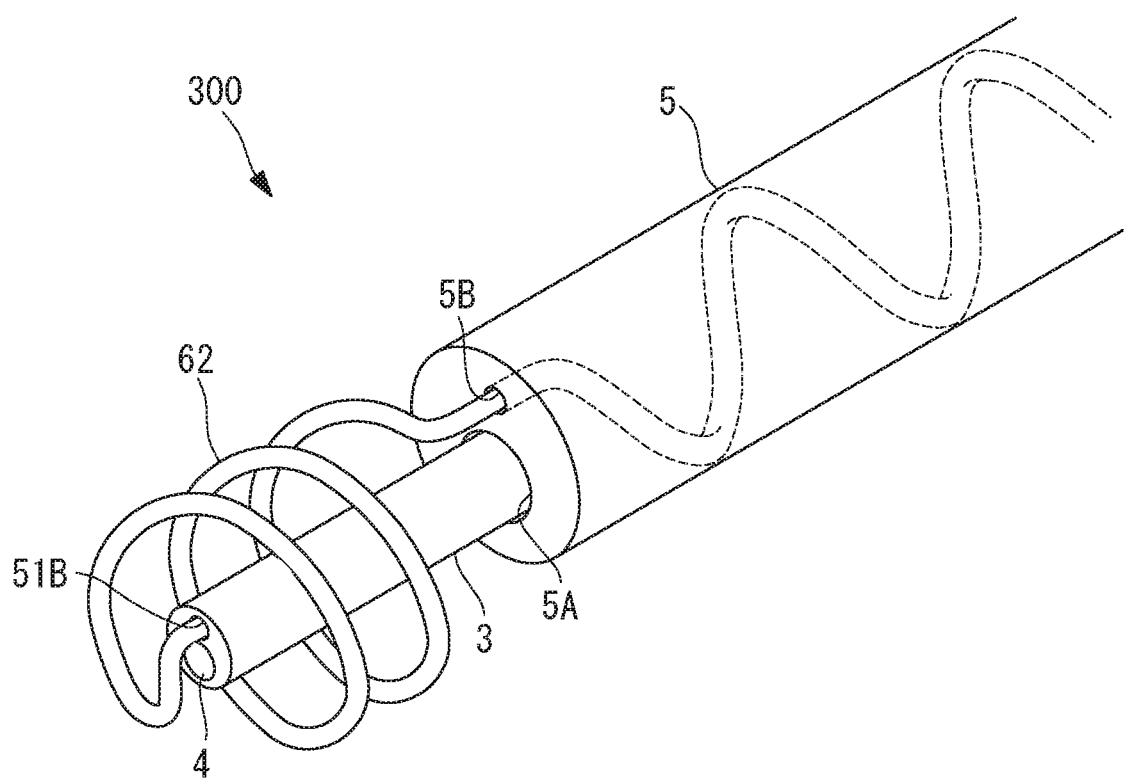
FIG. 20B is a perspective view showing the endoscope system in FIG. 20A when a wire is in an expanded form.

Although one of the linear regions 61 of the wire 6 is disposed in the gap between the outer circumferential surface of the insertion portion 3 and the inner circumferential surface of the endoscope insertion passage 5A of the sheath 5 in this embodiment, alternatively, as shown in FIGS. 20A and 20B, the sheath 5 may have a wire insertion passage 5B, which has been described in the first embodiment, and one of the linear regions 61 may be inserted into said wire insertion passage 5B. Although the wire insertion passage 5B may have a linear shape extending along the longitudinal direction of the sheath 5 as in the first embodiment, a spiral shape is preferable, as shown in FIGS. 20A and 20B.

Because the wire 6 is movable in the gap between the outer circumferential surface of the insertion portion 3 and the inner circumferential surface of the endoscope insertion passage 5A, it is difficult to efficiently transmit the pressing force applied to the end portions of the wire 6 up to the deforming region 62. In contrast, with this modification, because the movement of the wire 6 is restricted according to the shape of the wire insertion passage 5B, the pressing force applied to the end portions of the wire 6 is efficiently transmitted up to the deforming region 62. By doing so, it is possible to reliably expand the deforming region 62 into the expanded form.

Fourth Embodiment

Next, an endoscope system according to a fourth embodiment of the present invention will be described with reference to FIGS. 21A and 21B.

In the description of this embodiment, components that are different from those of the first embodiment will be mainly described, and components that are the same as those of the first embodiment will be assigned the same reference signs, and descriptions thereof will be omitted.

Figure 21A:
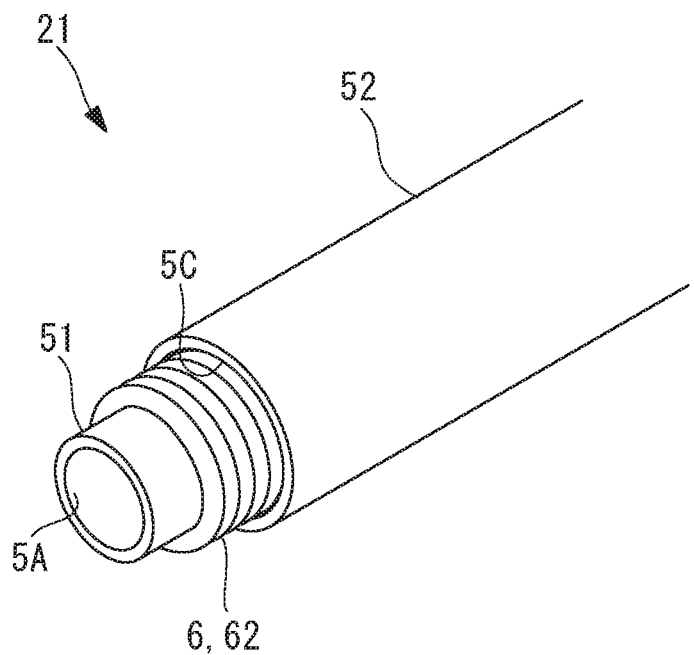
FIG. 21A is a perspective view showing the configuration of an endoscope device according to a fourth embodiment of the present invention.
Figure 21B:
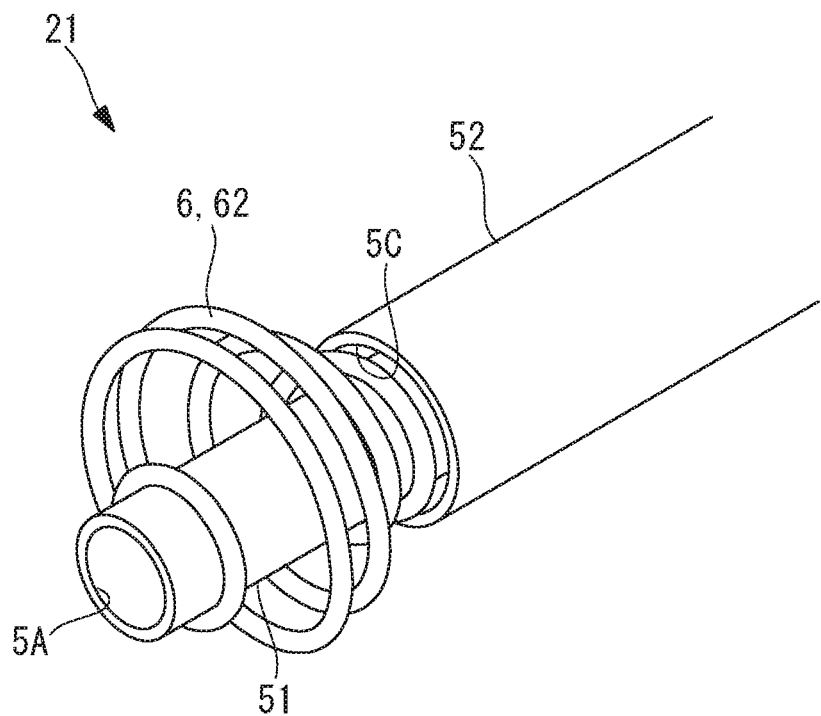
FIG. 21B is a perspective view showing the endoscope device in FIG. 21A when a wire is in an expanded form.

The endoscope system according to this embodiment differs from that in the first embodiment in that, as shown in FIGS. 21A and 21B, an endoscope device 21 is provided with a cylindrical first sheath 51 and a cylindrical second sheath (outer sheath) 52 that accommodates the first sheath 51 in the longitudinal direction thereof, and that a deforming region 62 of a wire 6 is spirally wound around the outer circumferential surface of a distal end portion of the first sheath 51.

The first sheath 51 has an endoscope insertion passage 5A that penetrates through the first sheath 51 in the longitudinal direction thereof, and that has openings on the distal end surface and the base end surface thereof.

The second sheath 52 has a sheath insertion passage 5C that penetrates through the second sheath 52 in the longitudinal direction thereof, and that has openings on the distal end surface and the base end surface thereof. The first sheath 51 inserted into the sheath insertion passage 5C can be rotated in either direction about the longitudinal axis of the first sheath 51. The distal end surface of the second sheath 52 is disposed at a position spaced apart from the distal end surface of the first sheath 51 to the base end side, and the outer circumferential surface of the distal end portion of the first sheath 51 is exposed.

The wire 6 has only the deforming region 62, which is spirally wound around the exposed distal end portion of the first sheath 51 along the outer circumferential surface of the first sheath 51. The deforming region 62 memorizes a spiral loop shape that has an outer diameter larger than the outer diameter of the second sheath 52, and that has a certain pitch in the longitudinal directions of the sheaths 51, 52.

The distal end of the deforming region 62 is fixed to the first sheath 51, and the base end of the deforming region 62 is fixed to the second sheath 52. Therefore, when the second sheath 52 is rotated with respect to the first sheath 51 in the same direction as the direction in which the deforming region 62 winds around the first sheath 51, as shown in FIG. 21A, the deforming region 62 deforms into a spiral-shaped normal form, in which the deforming region 62 comes into close contact with the outer circumferential surface of the first sheath 51 and winds around said outer circumferential surface. When the second sheath 52 is rotated with respect to the first sheath 51 in the direction opposite to the direction in which the deforming region 62 winds around the first sheath 51, as shown in FIG. 21B, the deforming region 62 deforms into a spiral-shaped expanded form having a larger diameter, with the first sheath 51 substantially at the center.

In this embodiment, the operator can cause deformation of the deforming region 62 between the normal form and the expanded form by rotating a base end portion of the second sheath 52 disposed outside the body. By doing so, there is an advantage in that it is possible to simplify the operation for deforming the deforming region 62, as compared to the case in which the two end portions of the wire 6 are pushed and pulled.

Because the other effects of this embodiment are the same as those of the third embodiment, descriptions thereof will be omitted.

As a result, the following aspect is read from the above described embodiment of the present invention.

A first aspect of the present invention is an endoscope device including: an elongated sheath having an endoscope insertion passage that penetrates therethrough in a longitudinal direction and into which an endoscope is inserted; and a wire that is provided in the sheath and that has a bending portion that bends toward the endoscope insertion passage, wherein the wire has a deforming region that is provided in a distal end portion of the sheath and that deforms between a normal form, in which the deforming region is disposed in the interior of the sheath or along an outer circumferential surface thereof, and a loop-shaped expanded form, in which the bending portion is bended and has a diameter larger than an outer diameter of the sheath.

With the first aspect of the present invention, it is possible to observe the interior of the pericardial cavity by using the endoscope by percutaneously placing the sheath into the interior of the pericardial cavity from outside the body, and by inserting the endoscope into the pericardial cavity via the endoscope insertion passage of the sheath.

In this case, the sheath is inserted into the pericardial cavity, in a state in which the deforming region of the wire is in the normal form, and the deforming region of the wire is subsequently deformed into the expanded form in the pericardial cavity. Because the deforming region in the expanded form, having an outer diameter larger than the outer diameter of the sheath, protrudes from the outer circumferential surface of the sheath in a radial direction thereof, the pericardium is held, by the deforming region in the expanded form, at a position separated from the distal end of the sheath, thereby forming a space in the vicinity of the distal end of the sheath where the distal end of the endoscope is disposed. By doing so, it is possible to ensure a sufficient viewing field of the endoscope in the pericardial cavity.

In the abovementioned first aspect, the sheath may have a wire insertion passage that is formed along the longitudinal direction, that has an opening on a distal end surface of the sheath or on an outer circumferential surface in the vicinity of a distal end thereof, and into which the wire is inserted so as to move in the longitudinal direction, and the deforming region may be provided in a distal end portion of the wire inserted into the wire insertion passage.

By doing so, it is possible to form a space in front of the distal end of the sheath by moving the wire to the distal end side to push out the deforming region from the opening of the wire insertion passage, and by deforming the deforming region into the expanded form. Furthermore, it is possible to adjust the size of the space in the longitudinal direction of the sheath by changing the protrusion amount of the deforming region from the wire insertion passage.

In the abovementioned first aspect, the sheath may have two of the wire insertion passages, the wire may have two linear regions, which each include an end portion of the wire, and the deforming region, which is positioned between the two linear regions, and the two linear regions may be inserted into the two wire insertion passages so that the deforming region is positioned on the distal end side.

By doing so, because the deforming region protruding from the distal end surface of the sheath is supported by the two linear regions in the wire insertion passages, it is possible to more stably hold the pericardium.

In the abovementioned first aspect, the expanded form may be such that the endoscope insertion passage is positioned substantially at the center thereof, when viewed in the longitudinal direction. In this case, the expanded form may have a circular shape or a polygonal shape.

By doing so, because the deforming region in the expanded form protrudes in all radial directions of the sheath, it is possible to form a space, by means of the deforming region, not only between the sheath and the pericardium but also between the sheath and the heart.

In the abovementioned first aspect, the deforming region may have a loop portion that forms a loop shape in the expanded form, wherein the bending portion is provided farther on the base end side than the loop portion and that bends in a direction intersecting a plane defined by the loop-shaped loop portion in the expanded form.

By doing so, when only the loop portion of the deforming region protrudes from the wire insertion passages, it is possible to form a space in front of the distal end of the sheath by using the loop portion protruding from the distal end surface of the sheath in the longitudinal direction thereof. In addition, when the bending portions also protrude from the wire insertion passages, the loop portion in the expanded form is placed in a direction intersecting with the outer surface of the heart by bending of the bending portions, and thus, it is possible to form a space larger than the outer diameter of the sheath between the outer surface of the heart and the pericardium.

In the abovementioned first aspect, a protrusion-amount control portion that is provided on the base end side of the sheath, and is configured to control a protrusion amount of the deforming region from the wire insertion passages to a prescribed amount may be provided.

By doing so, it is possible to appropriately control the protrusion amount of the deforming region from the wire insertion passages by means of the protrusion-amount control portion disposed outside the body.

In the abovementioned first aspect, an outer sheath that accommodates the sheath so as to rotate about a longitudinal axis of the sheath may be provided, the distal end portion of the sheath may be protruded and exposed from a distal end of the outer sheath, the deforming region may be spirally wound around an outer circumferential surface of the distal end portion of the sheath, a distal end of the deforming region may be fixed to the sheath, and a base end of the deforming region may be fixed to the outer sheath.

By doing so, by rotating the outer sheath in the same direction as the winding direction of the deforming region, it is possible to deform the deforming region into a normal form in which the deforming region is tightly wound around the outer circumferential surface of the sheath in a spiral manner. On the other hand, by rotating the outer sheath in the direction opposite to the winding direction of the deforming region, it is possible to deform the deforming region into a spiral-shaped expanded form having a larger diameter than the normal form.

A second aspect of the present invention is an endoscope system including: an endoscope having an elongated insertion portion that can be inserted into a body; and a wire that is provided in the insertion portion, wherein the wire has a deforming region that is provided in a distal end portion of the insertion portion and that is deformable between a normal form, in which the deforming region is disposed in the interior of the insertion portion or along an outer circumferential surface thereof, and a loop-shaped expanded form, which has a diameter larger than an outer diameter of the insertion portion.

REFERENCE SIGNS LIST

100, 200, 300 endoscope system
1 endoscope
2, 21 endoscope device
3 insertion portion
4 objective optical system
5, 51, 52 sheath
5A endoscope insertion passage
5B, 51B wire insertion passage
5C sheath insertion passage
6 wire
61 linear region
62 deforming region
62A loop portion
62B, 62C, 62D bending portion
7 protrusion-amount control portion (protrusion-amount controller)
A heart
B pericardium

The invention claimed is:
1. An endoscope device comprising:
an elongated sheath having an endoscope insertion passage that penetrates therethrough in a longitudinal direction and into which an endoscope is inserted, the elongated sheath being configured to be inserted into a pericardial cavity; and
a wire provided in the sheath, the wire having a bending portion that bends toward the endoscope insertion passage,
wherein the wire has a deforming region provided in a distal end portion of the sheath, the deforming region deforms between a normal form, in which the deforming region is disposed in a state of being accommodated in the interior of the sheath in a case in which the sheath is inserted into the pericardial cavity, and a loop-shaped expanded form, in which the bending portion is bended and the deforming region has a diameter larger than an outer diameter of the sheath, in a state in which the sheath reaches a desired position inside the pericardial cavity,
in the normal form, the deforming region of the wire is accommodated in the interior of the sheath except for a distal end of the deforming region, and
in the loop-shaped expanded form, a space in front of the endoscope is formed between a heart and a pericardium by expanding the deforming region so as to have the diameter larger than the outer diameter of the sheath.
2. The endoscope device according to claim 1, wherein the sheath has a wire insertion passage that is formed along the longitudinal direction, that has an opening on a distal end surface of the sheath or on an outer circumferential surface in the vicinity of a distal end thereof, and into which the wire is inserted so as to move in the longitudinal direction, and
the deforming region is provided in a distal end portion of the wire inserted into the wire insertion passage.

3. The endoscope device according to claim 2, further comprising a protrusion-amount controller that is provided on a base end side of the sheath, and is configured to control a protrusion amount of the deforming region from the wire insertion passage to a prescribed amount.

4. The endoscope device according to claim 1, wherein the expanded form is such that the endoscope insertion passage is positioned substantially at the center thereof, when viewed in the longitudinal direction.

5. The endoscope device according to claim 4, wherein the expanded form has a circular shape or a polygonal shape.

6. The endoscope device according to claim 1, wherein the deforming region has a loop portion that forms a loop shape in the expanded form,
  wherein the bending portion is provided farther on a base end side than the loop portion and that bends in a direction intersecting a plane defined by the loop-shaped loop portion in the expanded form.

7. The endoscope device according to claim 1, wherein
  the wire is configured to be advanced and retracted in a longitudinal direction,
  the sheath has an up-and-down direction and a left-and-right direction that are orthogonal to the longitudinal direction and that are orthogonal to each other,
  the wire further has a loop portion positioned on an upper side of the endoscope insertion passage and that, in the loop-shaped expanded form, expands in the left-and-right direction of the sheath, and
  the bending portion is provided farther on a base end side than the loop portion and bends the loop portion toward a lower side of the sheath.

8. The endoscope device according to claim 1, wherein
  the bending portion comprises a first bending portion provided farther on a base end side than a loop portion that forms a loop shape in the loop-shaped expanded form, and a second bending portion provided between the loop portion and the first bending portion,
  the first bending portion bends the loop portion toward an upper side of the sheath, and
  the second bending portion bends the loop portion toward a lower side of the sheath.

9. An endoscope system comprising:
an endoscope having an elongated insertion portion that can be inserted into a body; and
a wire provided in the insertion portion,
wherein the wire has a deforming region provided in a distal end portion of the insertion portion, the deforming region being deformable between a normal form, in which the deforming region is disposed in a state of being accommodated in the interior of the insertion portion in a state in which the sheath is inserted into a pericardial cavity, and a loop-shaped expanded form, in which the deforming region has a diameter larger than an outer diameter of the insertion portion, in a state in which the sheath reaches a desired position in the pericardial cavity,
in the normal form, the deforming region of the wire is accommodated in the interior of the insertion portion except for a distal end of the deforming region, and
in the loop-shaped expanded form, a space in front of the endoscope is formed between a heart and a pericardium by expanding the deforming region so as to have the diameter larger than the outer diameter of the sheath.

* * * * *